US007842850B2

(12) United States Patent
Singh

(10) Patent No.: US 7,842,850 B2
(45) Date of Patent: Nov. 30, 2010

(54) METHODS FOR PRODUCING FERTILE CROSSES BETWEEN WILD AND DOMESTIC SOYBEAN SPECIES

(75) Inventor: Ram J. Singh, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 655 days.

(21) Appl. No.: 11/417,369

(22) Filed: May 4, 2006

(65) Prior Publication Data

US 2007/0261139 A1  Nov. 8, 2007

(51) Int. Cl.
*A01H 1/00* (2006.01)
*A01H 1/02* (2006.01)
(52) U.S. Cl. ...................................... 800/268; 800/269
(58) Field of Classification Search .................. 800/260, 800/268, 269, 312
See application file for complete search history.

(56) References Cited

U.S. PATENT DOCUMENTS 5,710,365 A   1/1998   Kerr et al.

OTHER PUBLICATIONS

Newell et al. 1982. Crop Sci. 22: 1062-1065.*
Singh et al. 1987. Theor Appl Genet 74: 391-396.*
Singh et al. 1993. Crop Sci. 33: 1002-1007.*
Abe et al. (2003) "Photoperiod-Insensitive Japanese Soybean Landraces Differ at Two Maturity Loci," Crop Sci. 43:1300-1304.
Bodanese-Zanettini et al. (1996) "Wide Hybridization Between Brazilian Soybean Cultivars and Wild Perennial Relatives," Theor. Appl. Genet. 93(5-6):703-709.
Boote, K.J. (1980) "Double Cropping Soybean Succeeding Soybeans in Florida," Proceedings of the 3rd Annual Sothern Conservation Tillage Conference for Sustainable Agriculture, Jun. 19, 1980, Gainesville Florida, pp. 21-29.
Bromfield et al. (1980) "Resistance to Soybean Rust and Mode of Inheritance," Crop Sci. 20:254-255.
Bromfield, K.R. (1984) "Soybean Rust," monogr. 11, American Phytopathological Society, St. Paul, MN.
Bromfield et al. (1980) "Virulence and Aggressiveness of Cultures of Phakopsora pachyrhizi Causing Soybean Rust," Phytropath. 70:17-21.
Broué et al. (1982) "Interspecific Hybridization of Soybeans and Perennial Glycine Species Indigenous to Australia via Embryo Culture," Euphytica 31:715-724.
Brucker, E.A. (2004) "The Effect of the Soybean Gene rhg1 on Reproduction of Heterodera glycines in the Field and Greenhouse and Associated Effects on Agronomic Traits," M.S. Thesis, University of Illinois at Urbana-Champaign.
Burdon et al. (1981) "Inter- and Intra-Specific Diversity in Disease Response of Glycine Species to the Leaf Rust Fungus Phakospora pachyrhizi," J. Ecol. 69:381-390.
Burdon, J.J. (1986) "The Potential of Australian Native Glycine Species as Sources of Resistance to Soybean Rust (Phakopsora pachyrhizi)," In; New Frontiers in Breeding researches, Nampompeth et al. eds., Faculty of Agriculture, Kasetsart University, Bangkok, pp. 823-832.
Cheng et al. (1983) "Studies in Polyploidy in Soybeans: A Simple and Effective Colchicine Technique of Chromosome Doubling for Soybean (Glycine max (L.) Merr.) and its Wild Relatives," Soybean Genet. Newsl. 10:23-24.
Chung et al. (1990) "Production of Interspecific Hybrids Between Glycine max and G. tomentella Through Embryo Culture," Euphytica 48:97-101.
Chung et al. (1991) "Obtaining Intersubgeneric Hybridization Between Glycine max and G. Latifolia," Plant Tissue Culturing Technol. 18(1):39-45.
Coble et al. (1990) "Nutrient Culture Medium Components Affecting Plant Recovery from Immature Embryos of Three Glycine Genotypes and an Interspecific Hybrid Grown in Vitro," Euphytica 50:127-133.
Cook et al. (2000) "Cyst Nematodes: Globodera and Heterodera Species," In; Plant Resistance to Parasitic Nematodes, Starr et al. eds., CABI Publishing, pp. 71-105.
Croplan Genetics (2004) "Plant Characteristics," http://www.croplangenetics.com/soybean.asp?topic=4&sm=i_e.
Don et al. (1991) "Touch Down PCR to Prevent Spurious Priming During Gene Amplification," Nuc. Acids Res. 19:4008.
Doyle et al. (1985) "Numerical Analysis of Isozyme Variation in Glycine tomentella," Biochem. Syst. Evol. 13:413-419.

(Continued)

*Primary Examiner*—Medina A. Ibrahim
*Assistant Examiner*—Keith O. Robinson
(74) *Attorney, Agent, or Firm*—Greenlee, Winner and Sullivan, P.C.

(57) ABSTRACT

Methods for producing hybrids between domestic and wild soybean that are fertile and can be further bred with other soybean plants are provided, thus allowing transfer of desirable traits and genes from the wild soybean into the domestic soybean. This invention also provides novel media for producing callus and multiple somatic embryos, as well as novel media for producing multiple shoots from the embryos. The hybrid plants are made fertile by colchicine treatment to double their chromosome number so that they can be backcrossed into domestic soybean. These methods and media allow the production of elite soybean lines containing traits or genes from wild soybean as well as a minimum amount of additional wild soybean DNA. Backcrosses containing only one wild soybean chromosome can be produced, as well as sets of such backcrossed lines that each contain one chromosome from the wild ancestor, but collectively all the wild chromosomes from the hybrid ancestor. Plants and plant progeny and plant tissue (tissue including seeds) of plants produced by the foregoing methods are also provided. The methods do not require genetic modification, and thus this invention allows production of domestic soybean plants that are not genetically-modified organisms (non-GMO) but that express desirable traits derived from wild soybean.

39 Claims, 2 Drawing Sheets
(1 of 2 Drawing Sheet(s) Filed in Color)

OTHER PUBLICATIONS

Gamborg et al. (Apr. 1968) "Nutrient Requirements of Suspension Cultures of Soybean Root Cells," Exp. Cell Res. 50 (1):151-158.

Grant et al. (1986) "Cytogenetic Affinity Between the New Species Glycine argyrea and its Congeners," J. Heredity 77:423-426.

Harmon (2005) "Asian Soybean Rust Caused by Phakopsora pachyrhizi on Soybean and Kudzu in Florida," Online Plant Health Progress doi:10.1094/PHP-2005-0613-01-RS.

Hartman et al. (1991) "Soybean Rust Development and the Quantitative Relationship Between Rust Severity and Soybean Yield," Plant. Dis. 75:596-600.

Hartman et al. (1992) "Sources of resistance to Soybean Rust in Perennial Glycine Species," Plant Dis. 76(4):396-399.

Hartman et al. (2000) "Evaluation of Perennial Glycine Species for Resistance to Soybean Fungal Pathogens that Cause Sclerotinia Stem Rot and Sudden Death Syndrom," Crop Sci. 40:545-549.

Hartwig et al. (1983) "Relationship Among Three Genes Conferring Specific Resistance to Rust in Soybean," Crop Sci. 23:237-239.

Hartwig, E.E. (1986) "Identification of a Forth Major Gene Conferring Resistance to Soybean Rust," Crop Sci. 26:1135-1136.

Heath, M.S. (1989) "Analysis of Hybrid Plants and Progeny of a Cross Between Glycine max (L.) Merr. And Glycine tomentella," M.S. Thesis, Iowa State University.

Hood et al. (1980) "Interspecific Hybridization Studies Between Cultivated Soybean, Glycine max and a Perennial Wild Relative, G.falcata," Agron. Abst. American Society of Agronomy, Madison, WI., pp. 58.

Hood et al. (1987) "Crossing Soybeans with a Wild Perennial Relative," Tennessee Farm and Home Sci. 144:26-50.

Hymowitz, T. (1995) "I-D. Evaluation of Wild Perennial Glycine Species and Crosses for Resistance to Phakopsora," In; Proceedings of the Soybean Rust Workshop, Aug. 9-11, 1995, Sinclair et al. eds., National Soybean Research Laboratory Publication, No. 1, pp. 33-37.

Hymowitz et al. (1998) "The Genome of Glycine," In; Plant Breeding Reviews, Janick, J. ed., John Wiley and Sons, Inc., New York, pp. 289-317.

Hymowitz, T. (2004) "Speciation and Cytogenetics," In; Soybeans: Improvement, Production, and Uses, 3rd ed., Ch. 4, Agron. Monogr., No. 16, ASA, CSSA, SSSA, Madison, WI., pp. 97-136.

Hymowitz et al. (1984) "A Soybean X Glycine tomentella Hybrid: Progress and Problems," Soybean Gen. Newsl. 11:90.

Hymowitz et al. (1986) "Plant Regeneration from Leaf Explants of Glycine clandestine Wendl," Plant Cell Rep. 3:192-194.

Jena et al. (1989) "Monosomic Alien Addition Lines of Rice: Production, Morphology, Cytology, and Breeding Behavior," Genome 32:449-455.

Kameya et al. (1981) "Plant Regeneration from Hypocotyls Sections of Glycine Species," Plant Sci. Lett. 21:289-294.

Kartha, K.K. (1975) "Organogenesis and Embryogenesis," In; Plant Tissue Culture Methods, Gamborg et al. eds., National Research Council, Sasktoon, Canada, pp. 44-49.

Kenworthy, W.J. (1989) "Potential Genetic Contributions of Wild Relatives to Soybean Improvement," In; World Research Conference, Pascale, A.J. ed., proc., Buenos Aires, Mar. 5-9 Argentina, Assoc. Soja, Buenos Aires, pp. 883-888.

Kollipara et al. (1997) "Phylogenetic and Genomic Relationships in the Genus Glycine Willd. Based on Sequences from the ITS Region of Nuclear rDNA," Genome 40:57-68.

Kwon et al. (1991) "In Vitro Germination of Young Hybrid Embryos Between Glycine max and G. tomentella," Korean J. Breed. 22:379-383.

Ladizinsky et al. (1979) "Wide Crosses in Soybeans: Prospects and Limitations," Euphytica 28:421-423.

Livingston et al. (2004) "Economic and Policy Implications of Wind-Borne Entry of Asian Soybean Rust into the United States," USDA Outlook Report No. OCS04D02.

Mathew et al. (2000) "Differential Response of Soybean Yield Components to the Timing of Light Enrichment," Agronomy J. 92(1156-1161.

McWilliams et al. (1999) "Soybean Growth and Management Quick Guide," http://ext.nodak.edu/extpubs/plantsci/rowcrops/a1174/a1174w.html.

Meurer et al. (2001) "Embryogenic Response of Multiple Soybean [Glycine max (L.) Merr.] Cultivars Across Three Locations," In Vitro Cell Dev. Biol. Plant 37:62-67.

Morse et al. (1949) "Soybeans: Culture and Varieties," Department of Agriculture, Farmers' Bulletin, No. 1520, pp. 1-38.

Murashige et al. (1962) "A Revised Medium For Rapid Growth and Bioassays with Tobacco Tissue Cultures," Physiol. Plant. 15:473-497.

Newell et al. (1982) "Successful Wide Hybridization Between the Soybean and a Wild Perennial Relative, G. tomentella Hayata," Crop Sci. 22:1062-1065.

Newell et al. (1987) "Interspecific Hybrids Between the Soybean and Wild Perennial Relatives," J. Hered. 78:301-306.

Niblack, T. (2004) "SCN May be Causing Damage Greater that Expected in Southern Illinois," University of Illinois Extension Bulletin No. 19 Article 4.

Ogle et al. (1979) "Effect of Rust (Phakopsora pachyrhizi) on Soybean Yield and Quality in Southeastern Queensland, Australia," Aust. J. Agric. Res. 30:883-893.

Phillips et al. (1979) "In Vitro Tissue Culture of Selected Legumes and Plant Regeneration from Callus Cultures of Red Clover," Crop Sci. 19:59-64.

Rani et al. (2000) "Genetic Fidelity of Organized Meristem-Derived Micropropagated Plants: A Critical Reappraisal," In Vitro Cell Dev. Biol. Plant 36:319-330.

Riggs et al. (1998) "Possible Transfer of Resistance to Heterodera glycines from Glycine tomentella to Soybean," Supp. J. Nematol. 30(42):547-552.

Sakai et al. (1985) "Hybrid Embryo Formation in an Intersubgeneric Cross of Soybean (Glycine max Merrill.) With a Wild Relative (Glycine tomentella Hayata)," Jap. J. Breeding 35(4):363-374.

Schoen et al. (1992) "Resistance of Gycine tomentella to Soybean Leaf Rust Phakopsora pachyrhizi in Relation to Ploidy Level and Geographical Distribution," Theor. App. Genet. 83:827-832.

Shen et al. (1992) "Nodulation and Nodulin Gene Expression in an Interspecific Hybrid Between Glycine max and Glycine tomentella," Aust. J. Plant Physiol. 19(6):693-707.

Shoemaker et al. (1990) "Fertile Progeny of Hybridization Between Soybean (Glycine max (L.) Merr.) and Glycine tomentella Hayata," Theor. Appl. Genet. 80(1):17-23.

Sinclair, J.B. (1989) "Threats to Production in the Tropics: Red Leaf Biotch and Leaf Rust," Plant. Dis. 73:604-606.

Singh et al. (Nov. 1974) "Sources of Field Resistance to Rust and Yellow Mosaic Disease of Soybean," Ind. J. Genet. Plant Breed. 34(3):400-404.

Singh et al. (1985) "An Intersubgeneric Hybrid Between Glycine tomentella Hayata and the Soybean, G. max (L.) Merr.," Euphytica 34:187-192.

Singh et al. (1985) "The Genomic Relationships Among Six Wild Perennial Species of the Genus Glycine, subgenus Glycine Willd," Theor. Appl. Genet. 71:221-230.

Singh et al. (1987) "Intersubgeneric Crossability in the Genus Glycine Willd," Plant Breed. 98:171-173.

Singh et al. (1985) "Intra- and Interspecific Hybridization in the Genus Glycine Subgenus Glycine Willd: Chromosome Pairing and Genome Relationships," Z. Pflanzenzücht 95(4):289-310.

Singh et al. (1998) "Monosomic Alien Addition Lines Derived from Glycine max (L.) Merr. And G. tomentella Hayata: Production Characterization and Breeding Behavior," Crop Sci. 38:1483-1489.

Singh et al. (1993) "Backcross (BC2-BC4)-Derived Fertile Plants from Glycine max and G. tomentella Intersubgeneric Hybrids," Crop Sci. 33:1002-1007.

Singh et al. (1990) "Backcross-Derived Progeny from Soybean and Glycine tomentella Hayata Intersubgeneric Hybrids," Crop Sci. 30:871-874.

Singh et al. (1987) "Intersubgeneric Hybridization of Soybeans with a Wild Perennial Species, Glycine clandestine Wendl," Theor. Appl. Genet. 74:391-396.

Smith et al. (2001) "Temperature and Photoperiod Effects on Sterility in a Cytoplasmic Male-Sterile Soybean," Crop Sci. 41:702-704.

Tyagi et al. (2003) "Pollen from Glycine Species Survive Cryogenic Exposure," Cryolett. 24:119-124.

Tyagi et al. (2005) "High Frequency Plant Regeneration from an Amphiploid Hybrid Seed of Glycine max x G. tomentella Through Tissue Culture and Hybridity Testing of the Regenerants," Ind. J. Genet. 35(2):107-111.

Walbot, V. (1988) "Preparation of DNA from Single Rice Seedling," Rice Genet. Newsl. 5:149-151.

Widholm et al. (1983) "Shoot Regeneration from Glycine canescens Tissue Cultures," Plant Cell Rep. 2:19-20.

Wiebold, B. (Jul. 25, 2003) "Growth and Development of Soybeans: Flowering," Integrated Pest Crop Newsletter (University of Missouri-Coloumbia) 13(18):Article 2.

Zambre et al. (1998) "Plant Regeneration from Embryo-Derived Callus in Phaseolus vulgaris L. (Common Bean) and P. acutifolius A. Gray (Tepary Bean)," Plant Cell Rep. 17:626-630.

Zhang et al. (2001) "Effects of Photoperiod on Growth and Development of Soybean Floral Bud in Different Maturity," Agron. J. 93:944-948.

Zou et al. (2004) "SSR Marker and ITS Cleaved Amplified Polymorphic Sequence (CAPS) Analysis of Soybean x G. tomentella Intersubgeneric Derived Lines," Theor. Appl. Genet. 109:769-774.

Zou et al. (2003) "Assignment of Molecular Linkage Groups to Soybean Chromosomes by Primary Trisomics," Theor. Appl. Genet. 107:745-750.

* cited by examiner

METHODS FOR PRODUCING FERTILE CROSSES BETWEEN WILD AND DOMESTIC SOYBEAN SPECIES

FEDERAL FUNDING

This invention was made with Government support under Contract Numbers 2003-34488-13169 and 2004-34488-14456 awarded by the U.S.D.A. The Government has certain rights in the invention.

BACKGROUND

This invention Soybean is economically an important crop for feed, oil and other soy products. However, the genetic base of soybean cultivars grown in the United States is extremely narrow. Recent screening of domestic soybean varieties, plant introductions and other accessions at Ft. Detrick Maryland has shown all the varieties tested to have some level of susceptibility to soybean rust isolates recently collected from Asia, Africa, and South American. Most currently-available soybean varieties with sources of resistance to multiple strains of soybean cyst nematode are genetically similar, which indicates that finding new genes for resistance to soybean cyst nematode in domestic soybean germplasm may be difficult.

Soybean rust and cyst nematodes are economically damaging pathogens that threaten soybean production fields within the United States and elsewhere. Soybean rust (SBR) is a foliar soybean disease capable of causing significant economic yield loss (Bromfield, K. R. 1984, "Soybean Rust," Monogr. 11, American Phytopathological Society, St. Paul, Minn.; Ogle, H. J., D. E. Byth, and R. McLean, 1979, "Effect of rust (*Phakopsora pachyrhizi*) on soybean yield and quality in southeastern Queensland, Australia," Aust. J. Agric., Res. 30:883-893; Sinclair, J. B., 1989, "Threats to production in the tropics: Red leaf blotch and leaf rust," Plant Dis., 73:604-606). In recent years, soybean rust has reduced yields and raised production costs for soybeans in every major production region of the world except the United States. Two fungal species, *Phakopsora pachyrhizi* Sydow (also known as the Asian species) and *P. meibomiae* (Arthur) Arthur (also known as the New World species), cause soybean rust and are spread primarily by windborne spores that can be transported over long distances. Asian soybean rust, *P. pachyrhizi*, the more aggressive of the two species, was first reported in Japan in 1903 and was confined to the Eastern Hemisphere until its presence was documented in Hawaii in the mid-nineties. Soybean rust in the continental United States was first confirmed in November of 2004 (Harmon, P. F., M. T. Momol, J. J. Marois, H. Dankers, and C. L. Harmon, 2005, "Asian soybean rust caused by *Phakopsora pachyrhizi* on soybean and kudzu in Florida," Online Plant Health Progress, doi:10.1094/PHP-2005-0613-01-RS).

The number of states with confirmed soybean rust cases in the United States as of the end of 2005 stands at ten. The presence of soybean rust in Louisiana, Mississippi and Florida had been confirmed by USDA's Animal and Plant Health Inspection Service within a week of the initial discovery in Louisiana. Subsequent sampling resulted in confirmations of rust on soybeans in Alabama, Georgia, Arkansas, Missouri, South Carolina, Tennessee, and Texas. The species of soybean rust found on all positive samplings is Asian soybean rust (*P. pachyrhizi*), the more aggressive of the two species. The timing and distribution of soybean rust growth in the southeastern U.S. is consistent with spores having been brought from South American by Hurricane Ivan.

In the first year of a predicted soybean rust infestation, assuming that U.S. producers are able to treat with fungicides upon soybean rust detection, the expected value of losses across all U.S. agricultural producers and consumers would range from $640 million to $1,341 million, depending on the severity of infestation. U.S. soybean acreage would decline, and soybean prices to consumers would be expected to increase. (Livingston, M. et al. (2004) "Economic and Policy Implications of Wind-Borne Entry of Asian Soybean Rust into the United States," USDA Outlook Report No. OCS04D02.)

Four major resistance genes that confer specific resistance to *Phakopsora pachyrhizi* have been identified in *Glycine max* (Bromfield, K. R. and Hartwig, E. E., 1980, "Resistance to soybean rust and mode of inheritance," Crop Sci., 20:254-255; Hartwig, E. E. and Bromfield, K. R., 1983, "Relationship among three genes conferring specific resistance to rust in soybean," Crop Sci., 23:237-239; Hartwig, E. E., 1986, "Identification of a fourth major gene conferring resistance to soybean rust," Crop Sci., 26:1135-1136). However, isolates of *P. pachyrhizi* have been identified that are capable of causing a susceptible SBR type of reaction despite the presence of SBR resistance genes (Hartwig, E. E., 1986, "Identification of a fourth major gene conferring resistance to soybean rust," Crop Sci., 26:1135-1136). No general resistance or tolerance genes of SBR have been identified. The typical SBR resistant response consists of a few lesions that are red-brown in color and typically produce only small amounts of spores and in a fully susceptible reaction, more numerous tan colored lesions appear and produce profuse amounts of spores (Bromfield, K. R., Melching, J. S., and Kinsolver, C. H., 1980, "Virulence and aggressiveness of cultures of *Phakopsora pachyrhizi* causing soybean rust," Phytopath., 70:17-21). Application of fungicide is currently the only method of yield protection (Hartman, G. L., Wang, T. C., and Tschanz, A. T., 1991, "Soybean rust development and the quantitative relationship between rust severity and soybean yield," Plant Dis., 75:596-600).

Nematode infestations are also a significant problem for soybean production. These plant parasites are microscopic worms that cause 1.4 billion dollars in U.S. soybean crop losses annually. Nematodes are found ubiquitously in soybean crops. In most cases, damage caused by cyst nematode is not visually apparent, however, yield loss can still exceed 30% in the absence of foliar symptoms. Seventy percent of soil samples collected in southern Illinois were found to be positive for soybean cyst nematode (SCN, *Heterodera glycines Ichinoe*), with an average population density of 9,438 eggs per 100 cc of soil. This level of infestation is high enough to cause significant yield loss, even in known resistant varieties (Niblack, T. (2004), "SCN May Be Causing Damage Greater than Expected in Southern Illinois," University of Illinois Extension Bulletin No. 19 Article 4).

A soybean that is both rust-resistant and nematode-resistant is needed to improve crop yields.

The genus *Glycine* is divided into two subgenera—*Glycine* (perennials) and *Soja* (annuals). The commercial soybean is a member of the subgenus *Soja*, whose progenitor is the wild annual species *G. Soja*. The subgenus *Glycine* contains 26 wild perennial species (Singh, R. J. Nelson, R. L., and Chung, G. H. (2006), Soybean. In R. J. Singh (ed.) Genetic Resources, Chromosome Engineering, and Crop Improvement Oilseed Crops Volume 4. Taylor&Francis Group, Boca Raton, Fla., In press). These species have a wide geographical distribution, and are morphologically, cytologically and genomically diverse. Thus far, soybean breeders have been restricted to the subgenus *Soja* for improving soybean cultivars and have not exploited the wealth of genetic diversity found in the wild perennial *Glycine* species.

Wild perennial species of *Glycine* possess several useful agronomic traits (Burdon, J. J. and Marshal, D. R. (1981), "Inter- and intra-specific diversity in disease response of *Glycine* species to the leaf rust fungus *Phakospora pachyrhizi*," J. Ecol. 69:381-390; Burdon, J. J., 1986, "The potential of Australian native *Glycine* species as sources of resistance to soybean leaf rust (*Phakopsora pachyrhizi*)," p. 823-832 In B. Nampompeth and S. Subhadrabandu (eds) "New frontiers in breeding researches," Faculty of Agriculture, Kasetsart University, Bangkok; Hartman, G. L., Wang, T. C., and Hymowitz, T., 1992, "Sources of resistance to soybean rust in perennial *Glycine* species," Plant Dis., 76:396-399), including resistance to a number of fungal soybean diseases (Riggs, R. D., Wang, S., Singh, R. J., and Hymowitz, T., 1998, "Possible transfer of resistance to *Heterodera glycines* from *Glycine tomentella* to soybean," Supp. J. Nematol., 30(4S):547-552; Kenworthy, W. J., 1989, "Potential genetic contributions of wild relatives to soybean improvement," p. 883-888, In Pascale, A. J. (ed.), World Research Conference IV, Proc., Buenos Aires, 5-9 Mar. 1989, Argentina, Assoc. Soja, Buenos Aires; Hartman, G. L., Wang, T. C., and Hymowitz, T., 1992, "Sources of resistance to soybean rust in perennial *Glycine* species," Plant Dis., 76:396-399; Hartman, G. L., Gardner, M. E., Hymowitz, T., and Naidoo, G. C., 2000, "Evaluation of perennial *Glycine* species for resistance to soybean fungal pathogens that cause *sclerotinia* stem rot and sudden death syndrome," Crop Sci., 40:545-549; Schoen, D. J., Burdon, J. J., and Brown, A. H. D., 1992, "Resistance of *Glycine tomentella* to soybean leaf rust *Phakopsora pachyrhizi* in relation to ploidy level and geographical distribution," Theor. App. Genet., 83:827-832) and parasitic nematodes (Riggs, R. D., Wang, S., Singh, R. J., and Hymowitz, T., 1998, "Possible transfer of resistance to *Heterodera glycines* from *Glycine tomentella* to soybean," Supp. J. Nematol., 30(4S):547-552).

*Glycine tomentella* accessions PI441001 and PI441008 have been found to carry resistance to SBR (Schoen et al. (1992), supra), and SCN (Riggs et al. (1998), supra).

It would be beneficial to introduce these traits into cultivated soybean through wide hybridization. However, there are significant difficulties in utilizing wild perennials as a potential source of SBR resistance as the ploidy level between the two species are not necessarily comparable. A number of sterile intersubgeneric $F_1$ hybrids have been reported (Hymowitz, T. et al. (1998), "The genome of *Glycine*," In: Plant Breeding Reviews (ed. J. Janick), John Wiley and Sons, Inc., New York, USA:289-317).

Ladizinsky et al. (Ladizinsky, G., Newell, C. A., and Hymowitz, T. (1979), "Wide crosses in soybeans: prospects and limitations." Euphytica 28:421-423) attempted to hybridize domestic soybean with five species of wild soybean (*G. canescens, G. clandestine, G. falcata, G. tabacina*, and *G. tomentella*). However, they failed to produce viable $F_1$ hybrids.

Singh, R. J. et al. (1990), "Backcross-derived progeny from soybean and *Glycine tomentella* Hayata intersubgeneric hybrids," Crop Sci. 30:871-874, reported production, for the first time, of backcross-derived progenies from a synthetic amphiploid (2n=118, genome GGDDEE) of *G. max* (2n=40, genome GG)×*G. tomentella* Hayata (PI483218) (2n=78, genome DDEE). (The term "amphidiploid" is also used herein to refer to a plant having an artificially doubled chromosome number.) The objective was to obtain monosomic alien addition lines (MAALs) to study the introgression of genes from *G. tomentella* responsible for traits such as resistance to SBR, SCN, and tolerance to abiotic stresses (Singh, R. J., et al. (1998), "Monosomic alien addition lines derived from *Glycine max* (L.) Merr. and *G. tomentella* Hayata: Production, characterization and breeding behavior," Crop. Sci. 38:1483-1489). The frequency of seed formation and recovery of plants through immature hybrid embryo rescue was very low and only four pods were obtained from the amphidiploid plants. While backcrossing the amphidiploid (2n=118) with *G. max* cv. Clark 63 (2n=40), only 15 backcross plants with a chromosome number of 2n=76, instead of the expected chromosome number of 2n=79, were obtained. (Singh, R. J. et al. (1990), "Backcross-derived progeny from soybean and *Glycine tomentella* Hayata intersubgeneric hybrids," Crop Sci. 30:871-874.) No other workers have been able to duplicate the production of a fertile hybrid between a wild perennial and domestic soybean.

A summary of efforts to cross wild perennial soybean with domestic soybean to produce hybrids that can be used for further plant breeding is provided in Hymowitz, T. (2004), "Chapter 4, Specification and Cytogenetics" of Soybeans: Improvement, Production, and Uses, 3rd ed., Agronomy Monograph no. 16, American society of Agronomy, Crop Science Society of America, Soil Science Society of America, 677 S. Segoe Rd., Madison, Wis. 53711, USA. The only group which has been able to produce plants capable of breeding with elite domestic soybean lines for the purpose of introgressing useful traits from the wild species into high-yield domestic soybeans, has been that of the inventor.

Broué et al. (1982), "Interspecific hybridization of soybeans and perennial *Glycine* species indigenous to Australia via embryo culture. Euphytica 31:715-724, disclosed attempts to cross a hybrid between the wild perennial species *G. tomentella* and *G. canescens* with domestic *G. max*. The resulting plant was sterile.

In 1982, two crosses between wild perennial species *G. tomentella* and domestic *G. max* were reported, again producing only sterile plants (Newell, C. A. and T. Hymowitz (1982), "Successful wide hybridization between the soybean and a wild perennial relative, *G. tomentella* Hayata," Crop Sci. 22:1062-1065).

In 1985, Singh, R. J. and Hymowitz, T. (1985), "Intra- and Interspecific Hybridization in the Genus *Glycine* Subgenus *Glycine Willd*.: Chromosome Pairing and Genome Relationships," Z. Pflanzenzücht. 95(4): 289-310, showed that fertile hybrids could be obtained between certain wild perennial species. Due to the occurrence of pod abortion in distant hybrids, the immature seeds were extracted from the pods and germinated on an artificial medium. However, fertile plants capable of being backcrossed with domestic soybean were not obtained.

Sakai, T. and Kaizuma, N (1985), "Hybrid Embryo Formation in an Intersubgeneric Cross of Soybean (*Glycine max* Merrill.) with a Wild Relative (*Glycine tomentella* Hayata)," Japanese Journal of Breeding. 35(4): 363-374, reported production of a hybrid embryo cell in a cross between *G. max* and *G. tomentella*. No plant was produced.

Grant, J. E., et al. (1986), "Cytogenetic affinity between the new species *Glycine argyrea* and its congeners," Journal of Heredity 77, 423-426, reported crossing a hybrid between the wild species *G. argyrea* and *G. canescens* with domestic *G. max*, with chromosome amplification to produce an amphidiploid that was sterile.

Hood, M. J. and Allen, F. L. (1980), "Interspecific hybridization studies between cultivated soybean, *Glycine max* and a perennial wild relative, *G. falcata*," Agron. Abst. American Society of Agronomy, Madison, Wis. p. 58. and Hood, M. J. and Allen, F. L. (1987), "Crossing Soybeans with a wild perennial relative," Tennessee Farm and Home Science, 144:

26-50 reported attempts to cross *G. max* and the wild perennial *G. falcata*, but no hybrid plants were actually obtained (Hymowitz, T., 2004, "Speciation and cytogenetics," pp. 97-136, In Boerma, H. R. and Specht, J. E. (eds.), "Soybeans: Improvement, production and uses," 3$^{rd}$ ed., Agron. Monogr. 16 ASA, CSSA, and SSSA, Madison, Wis.). The plants observed were selfed plants rather than hybrids.

Singh, R. J., and Hymowitz, T. (1987), "Intersubgeneric crossability in the genus *Glycine Willd.*," Z. Pflanzenzüchtg 98:171-173, reported a sterile cross between domestic *G. max* and wild *G. clandestina*.

Also in 1987, Newell, C. A., et al. (1987), "Interspecific hybrids between the soybean and wild perennial relatives," J. Hered. 78:301-306, reported the first partially fertile cross between *G. tomentella* and *G. max*) after treatment of $F_1$ plants with colchicine. Additional crosses between *G. canescens* and *G. max*, and *G. tomentella* and *G. max*, after colchicine treatment, were sterile.

Shoemaker, R. C., et al. (1990), "Fertile Progeny of a Hybridization Between Soybean (*Glycine max* (L.) Merr.) and *Glycine tomentella* Hayata," Theoretical and Applied Genetics. 80(1): 17-23 reported that vegetative cuttings from the synthetic amphidiploid obtained from a cross between *G. max* and *G. tomentella* reported in Newell et al (1987)., supra, were transferred from the Monsanto Company to Iowa State University during October of 1987. However, this reputed hybrid was examined in a later thesis, Heath, M. S. (1989), "Analysis of Hybrid Plants and Progeny of a Cross Between *Glycine max* (L.) Merr. and *Glycine tomentella*," M. S. Thesis, Iowa State University, and it was discovered that the *G. tomentella* chromosome complement had been eliminated after genetic exchange and/or genetic modification had taken place between the two genomes. The purported hybridization could not be reproduced by the author or other researchers.

Coble, C. J. and Schapaugh, W. T. (1990), "Nutrient Culture Medium Components Affecting Plant Recovery from Immature Embryos of Three *Glycine* Genotypes and an Interspecific Hybrid Grown In Vitro," Euphytica. 50:127-133, reported a sterile *G. max*×*G. tomentella* cross.

Singh, R. J. et al. (1990), "Backcross-Derived Progeny from Soybean and *Glycine tomentella* Hayata Intersubgeneric Hybrids," Crop Sci. 30:871-874, reported that chromosomes of an $F_3$ hybrid, having 59 chromosomes, were doubled by colchicine treatment and the resulting amphidiploid was pollinated by soybean cultivars Altona, Bonus, Clark 63, Essex, Williams and Wye. The pollinated gynoecia were sprayed 24 hours after pollination with a hormone solution of 100 mg gibberellic acid (GA3), 25 mg 1-naphthalene acetic acid (NAA), and 5 mg kinetin/L distilled water. The $F_2$ plant yielded four pods with two seeds each. One seed was germinated to produce an $F_3$ plant that was multiplied by cloning and grafting onto the soybean. This was then crossed with domestic soybean cultivar Clark 63 to obtain three immature embryos from which 15 plants were regenerated through organogenesis from callus. These plants were pollen and seed sterile, and no second backcross generations were recovered. Five plants were similarly recovered from one callused embryo of the $F_3$ plant crossed with domestic soybean cultivar Essex. These plants contained 98 chromosomes and their use for further backcrossing was not reported.

Chung, G. H., and Kim, J. H. (1990) "Production of interspecific hybrids between *Glycine max* and *G. tomentella* through embryo culture," Euphytica 48:97-101, reported a sterile *G. max*×*G. tomentella* cross.

Chang, K. et al. (1991), "Interspecific Hybrids between *G. tomentella* and Soybean," Genetic Engineering Res. Inst. Report 6:23-38 (Korea), reported obtaining hybrid embryos; however, no fertile hybrids were reported.

Kim, K. S. (1991), "Obtaining Intersubgeneric Hybridization between *Glycine max* and *G. latifolia*," Plant Tissue Culturing Technology 18(1):3946 (Korea) reported hybridization, but no fertile hybrid plants.

Kwon, C. S. and Change, K. Y. (1991), "In vitro germination of young hybrid embryos between *Glycine max* and *G. tomentella*," Korean J. Breed. 22:379-383, reported production of a sterile hybrid.

Shen, B. H. and Davis, L. C. (1992), "Nodulation and Nodulin Gene Expression in an Interspecific Hybrid between *Glycine max* and *Glycine tomentella*," Australian Journal of Plant Physiology 19(6):693-707 reported hybridization but not fertile hybrids.

Singh, R. J., et al. (1993), "Backcross ($BC_2$-$BC_4$)-Derived Fertile Plants from *Glycine max* and *G. tomentella* Intersubgeneric Hybrids," Crop Sci 33:1002-1007, reported that the amphidiploid described above with respect to their 1990 paper was crossed with Clark 63 to form a first backcross ($BC_1$) plant, which was again crossed with Clark 63 to form a second backcross ($BC_2$) plant, and repeatedly backcrossed with Clark 63 to form $BC_3$-$BC_6$ plants.

Bodanse-Zanettini, M. H. et al. (1996) "Wide hybridization between Brazilian soybean cultivars and wild perennial relatives," Theoretical and Applied Genetics 93 (5-6):703-709, reported a cross between *G. max* and *G. tomentella* with colchicine treatment of the $F_1$ generation to produce an amphidiploid. Attainment of a fertile plant was not reported.

Singh, R. J. et al. (1998), "Monosomic alien addition lines derived from *Glycine max* (L.) Merr. and *G. tomentella* Hayata: production, characterization, and breeding behavior," Crop Sci. 38(6):1483-1489 reported that they had isolated 22 individual monosomic alien addition lines (MAALs) from fertile lines derived from the cross of *G. max* with *G. tomentella*. They also reported, in Riggs, R. D., et al. (1998), "Possible Transfer of Resistance to *Heterodera glycines* from *Glycine tomentella* to *Glycine max*," Supplement to Journal of Nematology 30(4S):547-552, that one of the seeds resulting from $BC_4$ plants reported in Singh, et al. (1993), was germinated and some of these plants were moderately resistant to nematodes of race 3, one of the crosses was resistant to race 5 in a single test, and four were resistant and five moderately resistant to race 14. None were resistant to all three races. However, Brucker, E. A. (2004), "The Effect of the Soybean Gene rhg1 on Reproduction of *Heterodera glycines* in the Field and Greenhouse and Associated effects on Agronomic Traits," MS Thesis, University of Illinois at Urbana-Champaign, found no resistance in the backcross generations.

All publications and patent documents referred to herein are incorporated by reference to the extent not inconsistent herewith.

SUMMARY OF THE INVENTION

The genus *Glycine Willd.* is divided into two subgenera— *Glycine* (perennial) and *Soja* (Moench) F. J. Herm. (annual). The commercial soybean is a member of the subgenus *Soja*, whose progenitor is the wild annual species *G. Soja*. The subgenus *Glycine* contains 26 wild perennial species (Singh, R. J. Nelson, R. L., and Chung, G. H. (2006) Soybean. In R. J. Singh (ed.) Genetic Resources, Chromosome Engineering, and Crop Improvement Oilseed Crops Volume 4. Taylor & Francis Group, Boca Raton, Fla., In press). Many of the wild perennial species carry valuable agronomic traits. However, as is evidenced by the many failed attempts described above, the wild and domestic species do not readily hybridize with each other to produce fertile plants. This is essential if the valuable traits from the wild species are to be bred into domestic soybean varieties.

This invention provides methods for producing hybrids between domestic and wild perennial soybean that are fertile and that can be further bred with other soybean plants. In this way, desirable traits and genes present in the wild soybean can be transferred into the domestic soybean. Thus domestic soybeans containing desirable traits from wild soybean can be produced without genetic modification.

The methods include novel procedures. Novel media are also provided for culturing immature hybrid seeds to produce callus and multiple somatic embryos, as well as for producing multiple shoots from the embryogenic callus. The hybrid plants produced by this method can be made fertile by doubling their chromosome number. They can then be backcrossed with domestic soybean cultivars.

Embodiments of this invention include the production of elite soybean lines containing traits or genes from wild soybean as well as a minimum amount of additional wild soybean DNA. A "minimal" amount is defined in this context as meaning that no undesirable effects are produced by the wild soybean DNA that is transferred to the domestic soybean along with the desired genes.

This invention further provides methods for producing backcross generations of the hybrid plants with domestic soybean, and plants that have only one wild soybean chromosome. This invention also provides a set of such backcross generations containing only one wild soybean chromosome, wherein each plant in the set contains a different wild soybean chromosome. A preferred set of such plants collectively contains all the chromosomes derived from the wild parent that were present in the hybrid $F_1$ plant ancestral to the plants in the set, each plant in the set containing a different wild soybean chromosome.

Plants and plant progeny and plant tissue (tissue including seeds) of plants produced by the foregoing methods are also provided by this invention.

BRIEF DESCRIPTION OF THE FIGURES

This patent or application file contains at least one drawing executed in color. Copies of this patent or patent application publication with color drawing(s) will be provided by the Office upon request and payment of the necessary fee.

DETAILED DESCRIPTION

Figure 1:
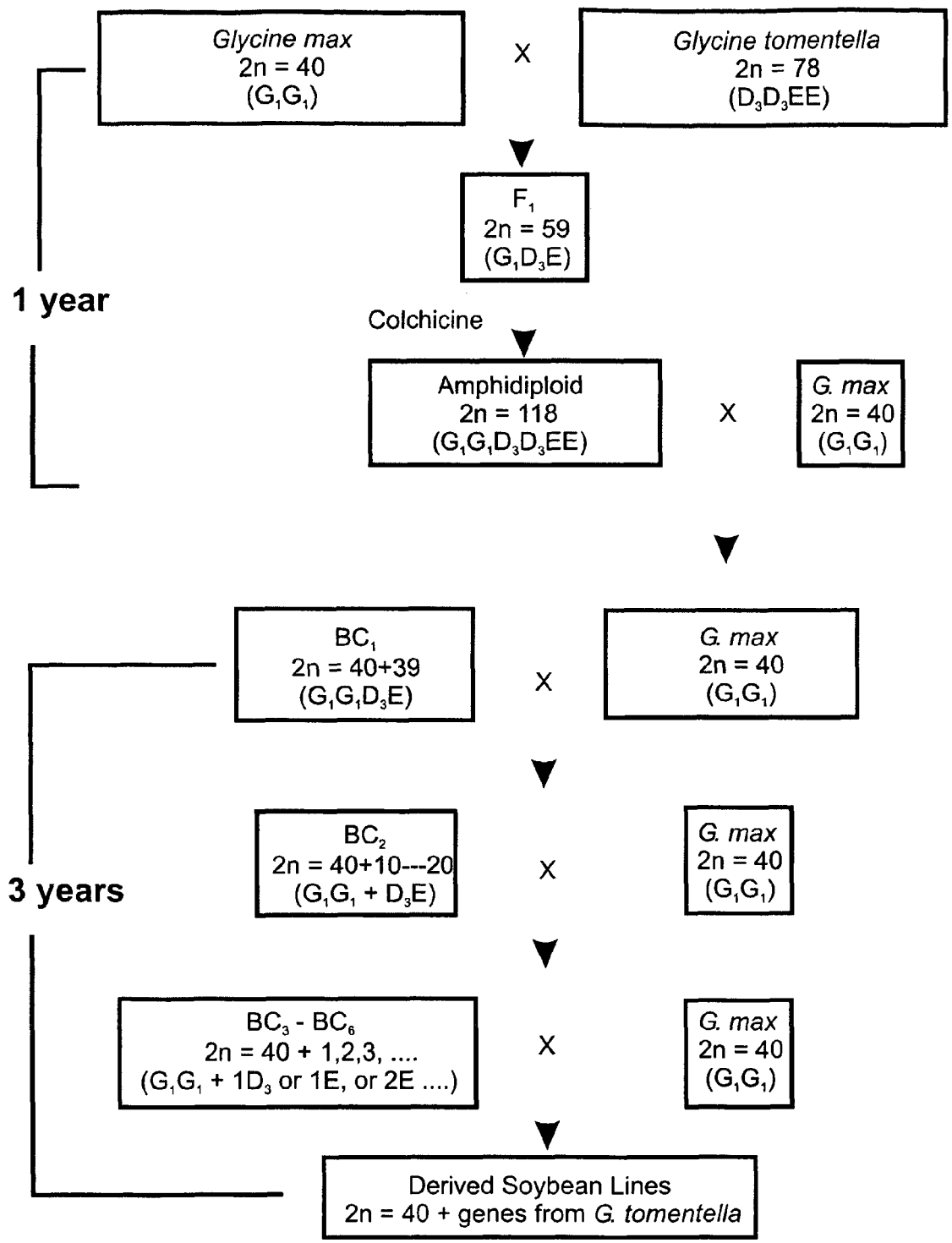
FIG. 1 is a schematic diagram showing the methods of this invention for producing hybrids between wild perennial *Glycine* species and domestic annual soybean cultivars.

As shown in FIG. 1, this invention provides a scheme for introgressing genes from wild perennial *Glycine* species (also referred to herein as "wild soybean") into domestic annual *Glycine* cultivars (also referred to herein as "domestic soybean"). The method includes crossing (designated by the "X" in the Figure) a domestic soybean, designated "*Glycine max*" in the Figure with a wild soybean, designated "*Glycine tomentella*" in the Figure. Although the scheme illustrates the invention with reference to this particular wild soybean species, other wild soybean species can be substituted for *Glycine tomentella*.

*Glycine max* has 40 chromosomes (2n=40), and a $G_1G_1$ genome, more fully explained below. As is known in the art, the *Glycine tomentella* accessions PI441001 and PI441008 used to illustrate the invention have 78 chromosomes (2n=78), and a genome $D_3D_3EE$. Other *Glycine tomentella* accessions have differing numbers of chromosomes and different genomes.

As shown by the first down arrow in FIG. 1, the cross produces an $F_1$ hybrid having 59 chromosomes (2n=59) and a genome ($G_1D_3E$). The hybrid has inherited half the total number of chromosomes present in each parent, 20 chromosomes from the domestic soybean parent and 39 from the wild soybean parent. These hybrid plants may be screened to identify plants that have retained desirable traits and/or genes from the wild parent plants for further breeding.

The hybrid plants are treated with colchicine to double their chromosome number to 118 (2n=118) in order to make them fertile. Forty of these chromosomes are domestic soybean chromosomes and 78 are wild soybean chromosomes. The plants with doubled chromosome number are called "amphidiploid" plants herein. They have two copies of the chromosomes making up the original hybrid genome ($G_1G_1D_3 D_3EE$). Again, the amphidiploid plants can be screened to identify plants that have retained desirable traits and/or genes for further breeding.

The amphidiploid plants are then backcrossed with *G. max* to produce a first backcross ($BC_1$) generation. Plants of this $BC_1$ generation have 79 chromosomes, representing half the chromosomes of each parent: 20 domestic soybean chromosomes inherited from the domestic soybean parent, 20 domestic soybean chromosomes inherited from the amphidiploid plant for a total of 40 domestic soybean chromosomes, and 39 wild soybean chromosomes. The genome of the $BC_1$ plants is $G_1G_1D_3E$. Cytological examination shows the domestic soybean chromosomes to be paired in the center of the cells, and the wild soybean chromosomes to be unpaired and floating free toward the poles. The plants can be screened to verify plants retaining desirable traits from wild perennial soybean and/or genes for further breeding.

The $BC_1$ generation of plants is then further backcrossed with *G. max* to produce a second backcross ($BC_2$) generation. Each plant of this $BC_2$ generation will have an indeterminate number of chromosomes, 20 domestic soybean chromosomes from each parent for a total of 40 domestic soybean chromosomes, and 10 to 20 from the wild soybean parent. $BC_2$ plants must be tested to determine the presence of the wild soybean genes. The genome of these $BC_2$ plants will again be ($G_1G_{1+}$ various combinations of $D_3E$). The $BC_2$ plants can be screened to identify plants that have retained desirable traits and/or genes for further breeding.

The $BC_2$ plants are then further backcrossed with *G. max* to produce a third backcross ($BC_3$) generation. Due to further loss of unpaired wild soybean chromosomes during meiosis, each $BC_3$ plant will have an indeterminate, lesser number of chromosomes, still retaining 40 domestic soybean chromosomes and 1, 2, 3, or more wild soybean chromosomes. The genome will be $G_1G_1$ (from the domestic soybean) plus one or more chromosomes of genome $D_3$ or $E$ inherited from the wild soybean. Again the $BC_3$ plants can be screened to identify plants that have retained desirable traits and/or genes for further breeding.

The object of this method is to produce a domestic soybean variety that can express desirable agronomic traits inherited from the wild soybean ancestor. To that end, $BC_2$ plants having only one wild soybean chromosome and carrying genes for a desirable trait are valuable. Knowing which wild soybean chromosome carries a desired gene allows fast identification of plants bearing the gene and also identification and isolation of the gene so that it can be chromosomally engineered into elite soybean lines. In one aspect of this invention, a set of plants is produced wherein each plant carries a different single wild soybean chromosome. When an original wild soybean parent carrying 78 chromosomes is used, as exemplified herein, 39 different plants are required, each having a different wild soybean chromosome. When the original wild soybean parent carries a different number of chromosomes, the number of plants required for the set will again be half the original number of chromosomes. These plants can be screened for desirable traits from the wild soybean, thus identifying which wild soybean chromosome carries which trait.

In a further aspect of this invention, backcrossed plants having a desirable trait derived from wild soybean on a single wild chromosome present in the plant can be irradiated or otherwise treated, for example, by chemical mutagens such as ethylmethane sulphonate (EMS) or sodium azide, to increase the likelihood of recombination of genetic material into a domestic soybean chromosome, then further bred until the wild soybean chromosome is lost, thereby producing a domestic soybean carrying the trait without extraneous wild soybean DNA.

To obtain plants carrying the desirable trait from wild soybean and a minimum amount of additional wild soybean DNA, the $BC_2$ plants can be further backcrossed with *Glycine max* to produce third through sixth backcross generations ($BC_3$-$BC_6$). At each generation plants are screened for the presence of the desirable trait to identify plants suitable for further breeding.

Production of wild/domestic soybean hybrids has been an extremely difficult undertaking, and to date no reliable method has been known for producing hybrids that can be backcrossed with domestic soybean. This invention provides such methods. Because each of the early steps (production of hybrid plants, production of fertile amphidiploid and first backcross plants) is difficult and has a low success rate, it is desirable to produce large numbers of plants at each step.

This invention provides a method for producing at least one hybrid, and preferably multiple hybrids, between a first parent plant of a wild perennial *Glycine* species and a second parent plant that is a domestic annual *Glycine* cultivar. The method comprises: (a) providing a plurality of first and second parent plants; (b) allowing the parent plants to flower; (c) emasculating flowers of one of said first or second parent plants and fertilizing said emasculated flowers with pollen from the other of said first or second parent plants; (d) obtaining at least one immature seed from a pod resulting from said fertilized flowers; (e) culturing said seed on a seed maturation medium comprising sufficient growth hormones to prevent seed germination and produce callus; (f) culturing embryos produced by said callus on a multiple shoot-regeneration medium to produce shoots; (g) rooting said shoots to form plantlets, and hardening said plantlets to form hybrid plants.

Domestic *Glycine* cultivars useful for hybridization to wild perennial *Glycine* species include a huge number of cultivars, for example, those publicly available through the United States Department of Agriculture active collection located in Urbana, Ill. Some of the more useful cultivars include Dwight, Ina, Macon, Williams 82, and Clark 63. Soybean cultivars selected for their ease of hybridization to other varieties that were used to exemplify this invention, were Dwight, Macon, and Ina.

Wild perennial *Glycine* species useful in this invention can be selected from all the species known to exist, which have been collected in diverse locations including Australia and the Pacific Basin including Taiwan, the Philippines and South Pacific Islands. Most of these species are publicly available through the United States Department of Agriculture active collection located in Urbana, Ill. The more useful species include those known to carry agronomically valuable traits, such as *Glycine tomentella* (2n=78) PI441001 which carries resistance to SBR and SCN, and *G. tomentella* (2n=78) PI441008, which carries resistance to SBR and SCN.

Desirable agronomic traits present in wild perennial soybean species include resistance to SCN, SBR, bean pod mottle virus (BPMV) and aphid.

Wild *Glycine* species that may be used in this invention include *G. canescens*, *G. argyrea*, *G. clandestine*, *G. latrobeana*, *G. albicans*, *G. aphyonota*, *G. arenaria*, *G. curvata*, *G. cyrtoloba*, *G. dolichocarpa*, *G. falcata*, *G. gracei*, *G. hirticaulis*, *G. lactovirens*, *G. latifolia*, *G. microphylla*, *G. montis-douglas*, *G. peratosa*, *G. pescadrensis*, *G. pindanica*, *G. pullenli*, *G. rubiginosa*, *G. stenophita*, *G. syndetika* and *G. tabacina*. *G. tomentella* (2n=38; 40, 78, and 80) including PI441001 and PI441008 are known to be highly resistant to SBR and SCN and are useful wild *Glycine* species for breeding with domestic soybean in accordance with this invention.

The wild perennial *Glycine* species preferably has a genome selected from the group consisting of A, D and E genomes, and combinations thereof. The ability of a given wild perennial species to cross with another species determines its genome designation. When hybrids between two species are fertile they are given the same genome symbol. Wild perennial *Glycine* species are isolated by geography and paracentric inversions. When crosses between species result in inviable germination, lethals, or collapse prior to flowering, they are given separate genome symbols. Early work by Singh, R. J. and Hymowitz, T. (1985) "The genomic relationships among six wild perennial species of the genus *Glycine*, subgenus *Glycine Willd.*," Theor. Appl. Genet. 71:221-230, and subsequent research assigned genome symbols to the wild perennial species as set forth in Table 1.

TABLE 1

Taxonomy and Properties of the *Glycine* Species

| Species | 2n | Nuclear Genome Symbol[1] | Chloroplast Genome Symbol[2] | USDA Plant Introduction (PI) Accession number | Australian Accession Number | Distribution[3] |
| --- | --- | --- | --- | --- | --- | --- |
| Subgenus *Glycine* | | | | | | |
| 1. *G. albicans* Tindale and Craven | 40 | I | A | | 2049 | Aust.: WA |
| 2. *G. aphyonota* B. Pfeil | 40 | $I_3$ | A | | 2589 | Aust.: WA |
| 3. *G. arenaria* Tindale | 40 | H | A | 505204 | 1305 | Aust.: WA |
| 4. *G. argyrea* Tindale | 40 | $A_2$ | A | 505151 | 1420 | Aust.: Q |

TABLE 1-continued

Taxonomy and Properties of the *Glycine* Species

| Species | 2n | Nuclear Genome Symbol[1] | Chloroplast Genome Symbol[2] | USDA Plant Introduction (PI) Accession number | Australian Accession Number | Distribution[3] |
|---|---|---|---|---|---|---|
| 5. *G. canescens* F. J. Hermann | 40 | A | A | 440932 | 1853 | Aust.: Q, NSW, V, SA, NT, WA |
| 6. *G. clandestina* Wendl. | 40 | $A_1$ | A | 440958 | 1126 | Aust.: Q, NSW, V, SA, T |
| 7. *G. curvata* Tindale | 40 | $C_1$ | C | 505166 | 1849 | Aust.: Q |
| 8. *G. cyrotoloba* Tindale | 40 | C | C | 440962 | 1184 | Aust.: Q, NSW |
| 9. *G. falcata* Benth. | 40 | F | A | 505179 | 1155 | Aust.: Q, NT, WA |
| 10. *G. gracei* B. E. Pfeil and Craven | 40 | | | | 3124 | Aust.: NT |
| 11. *G. hirticaulis* Tindale and Craven | 40 | $H_1$, | A, (A) | IL1246 | 2876 | Aust.: NT |
| | 80 | | | IL943 | 1956 | Aust.: NT |
| 12. *G. lactovirens* Tindale and Craven | 40 | $I_1$ | A | IL1247 | 2720 | Aust.: WA |
| 13. *G. latifolia* (Benth.) Newell and Hymowitz | 40 | $B_1$ | B | 378709 | 1697 | Aust.: Q, NSW |
| 14. *G. latrobeana* (Meissn.) Benth. | 40 | $A_3$ | A | 483196 | 1385 | Aust.: V, SA, T |
| 15. *G. microphylla* (Benth.) Tindale | 40 | B | B | 440956 | 1867 | Aust.: Q, NSW, V, SA, T |
| 16. *G. montis-douglas* B. E. Pfeil and Craven | 40 | | | | | Aust.: NT |
| 17. *G. peratosa* B. E. Pfeil and Tindale | 40 | $A_5$ | A | | 2916 | Aust.: WA |
| 18. *G. pescadrensis* Hayata | 80 | $AB_1$ | A | 440996 | 1433 | Aust.: Q, NSW; Taiwan, Japan |
| 19. *G. pindanica* Tindale and Craven | 40 | $H_2$ | A | 595818 | 2951 | Aust.: WA |
| 20. *G. pullenii* B. Pfeil, Tindale and Craven | 40 | $H_3$ $A_4$ | A | | 2599 | Aust.: WA |
| 21. *G. rubiginosa* Tindale and B. E. Pfeil | 40 | $B_3$ | A | 440954 | 1874 | Aust.: NSW, SA, WA |
| 22. *G. stenophita* B. Pfeil and Tindale | 40 | | B | 378705 | 2600 | Aust.: Q, NSW; (Japan?) |
| 23. *G. syndetika* B. E. Pfeil and Craven | 40 | | | 441000 | 1300 | Aust.: Q |
| 24. *G. dolichocarpa* Tateishi and Ohashi | 80 | $D_1A$ | | | | Taiwan |
| 25. *G. tabacina* (Labill.) Benth. | 40 | $B_2$ | B | 373990 | 1317 | Aust.: Q, NSW |
| | 80 | $BB_1$; $BB_2$; $B_1B_2$ | B | 373992 | 1314 | Aust.: Q, NSW, V, SA; West Central and South Pacific Islands |

| | Isozyme Group[4] | | | | | | |
|---|---|---|---|---|---|---|---|
| 26. *G. tomentella* Hayata | $D_1$, $D_2$ | 38 | E | A | 440998 | 1858 | Aust.: Q |
| | $D_3$ | 40 | D | A | 505222 | 1749 | Aust.: Q, WA, PNG |
| | $D_5B$ | 40 | $H_2$ | A | 505294 | 1943 | Aust.: WA |
| | $D_5A$ | 40 | $D_2$ | A | 505203 | 1303 | Aust.: WA, NT |
| | $T_1$ | 78 | $D_3E$ | A | 441001 | 1133 | Aust.: Q, NSW; PNG |
| | $T_5$ | 78 | AE | A | 509501 | 1487 | Aust.: NSW |
| | $T_6$ | 78 | E $H_2$ | A | 505286 | 1945 | Aust.: WA |
| | $T_2$ | 80 | D $A_6$ | A | 441005 | 1188 | Aust.: Q; Taiwan |
| | $T_3$ | 80 | D $D_2$ | A | 483219 | 1927 | Aust.: Q, NT, WA; PNG; Timor |
| | $T_4$ | 80 | $H_2$ | A | 330961 | 1348 | Aust.: Q, NT, WA; Philippines, Taiwan |

Subgenus *Soja* (Moench) F. J. Hermann

| Species | 2n | Nuclear Genome Symbol[1] | Chloroplast Genome Symbol[2] | USDA Plant Introduction (PI) Accession number | Australian Accession Number | Distribution[3] |
|---|---|---|---|---|---|---|
| *G. soja* Sieb. & Zucc. | 40 | G | G | 51762 | | China, Japan, Russia, Korea, Taiwan |
| *G. max* (L.) Merr. | 40 | $G_1$ | G | | | Cultigen; worldwide |

[1]Genome symbols were assigned to species based on cytogenetics and molecular techniques such as sequencing of ITS region of satellite chromosome of soybean and wild perennial *Glycine* species (Kollipara, K. P., R. J. Singh, and T. Hymowitz (1997) "Phylogenetic and genomic relationships in the genus *Glycine* Willd. based on sequences from the ITS region of nuclear rDNA," Genome 40: 57-68.
[2]Chloroplast genome; J. J. Doyle personal communication
[3]Distribution abbreviation; Aust., Australia; WA, Western Australia; Q, Queenslands; NT, Northern Territory; SA, South Australia; T, Tasmania; V, Victoria; NSW, New South Wales; PNG, Papua New Guinea
[4]Isozyme groups were assigned by Doyle, M. J. and A. H. D. Brown (1985) "Numerical analysis of isozyme variation in *Glycine tomentella*. Biochem. Syst. Evol. 13: 413-419.; A. H. D. Brown, personal communication.
G number kindly provided by A. H. D. Brown By convention, the genome symbol GG is reserved for the domestic soybean and its wild annual ancestor *Glycine soja*. Of the available wild perennial *Glycine* species, the species having A, D, and E genomes are closest to the soybean genome G. The presence of these genomes therefore identifies a class of preferred wild perennial species for crossing with domestic soybean. All the published hybridizations of the soybean with the wild perennial *Glycine* species (described above in the Background section) used A, D and/or E genome combinations.

Some plants will flower under ordinary greenhouse conditions; however, for plants originating in tropical regions where day length is less than about thirteen hours, it may be necessary to limit the amount of light the plants receive to thirteen hours or less, for example, eight hours, to induce flowering. This can be done by placing a black cloth over the plants at the end of the work day (5:00 PM) and removing at the beginning of the work day (8:00 AM). It was not necessary to use the black cloth procedure to induce flowering of the wild perennial species exemplified herein. It is best not to use the first flush of flowers, as pod abortion is about 100% using the first flush. Using the second flush of flowers, pod set is about 50%.

The domestic soybean can be used as the female parent and the wild perennial species as the male parent, or vice versa. The emasculation of the domestic soybean plants to be used as female parents must be very carefully done to avoid damage to the gynoecium and self pollination. These flowers are two times smaller than wild soybean flowers. Similarly, when the wild plants are used as the male parents, care must be taken to avoid damage to the gynoecium and self pollination. Details of the procedures used are provided in the Examples.

The fertilized plants rarely produce pods. Only about 1% of the pollinated flowers produced pods in the hybridization experiments reported herein. Thus it is important to begin with a large enough number of parent plants to be sure of obtaining at least a single hybrid pod containing a seed.

After fertilization it is important to check the plants often, and to mark all pods that are spotted so they can be kept track of. The hybrid pods are dark green and must be distinguished from occasional selfed pods that occur. When the domestic soybean is the female parent, the selfed pods will be yellow-green in color and about four times larger than the hybrid pods. When the wild perennial species is the female parent, the selfed pods will be green in color and about three times larger than the hybrid pods. Early pod abortion is common and can be ameliorated by spraying with hormones as described in the Examples to inhibit the abscission layer. Suitable growth hormones for this purpose are known to the art. Such growth hormones can be selected from the group consisting of gibberellic acid ($GA_3$), 1-naphthalene acetic acid (NAA) and kinetin (K), and combinations thereof.

After 19 to 21 days, the hybrid pods are removed from the plant and surface sterilized, immature seeds are extracted and placed on the novel seed maturation (SM) medium of this invention, which contains growth hormones to allow the production of callus rather than germination of the single seed. The callus will produce multiple embryos, whereas germination will allow production only of a single plant from each seed.

The growth hormones in the seed maturation medium should be present in type(s) and amount(s) sufficient to prevent germination and foster callus production. Preferably, the growth hormones for the SM medium are selected from the group consisting of indole acetic acid (IAA) or gibberellic acid ($GA_3$), 1-naphthalene acetic acid (NAA), benzylaminopurine (BAP), kinetin and combinations of any of the foregoing. The amount of growth hormone used should be about 0.4 mg/L IAA or $GA_3$, 4 mg/L NAA, and 1.3 mg/L kinetin. These optimal amounts can vary in accordance with preparation procedures, typically around 0.1 mg/L. Too little growth hormone will prevent embryo development. Too much growth hormone will cause embryo death.

The medium used to produce callus should contain (a) major salts; (b) minor salts; (c) iron; (d) vitamins; (e) growth hormones; (f) sugar; and (g) a medium such as gel rite or agar. For best results, the pH should be around neutral (about 5.6 to about 6).

Table 2 provides the composition of the preferred SM medium of this invention, as well as a preferred shoot regeneration medium (Singh C5 medium), and for comparison purposes also provides the composition of the commercial media, Murashige and Skoog medium (MS) and Gamborg B5 medium (B5). As will be appreciated by those skilled in the art, media constituents and amounts given in Table 2 are optimal, but can be varied by those of skill in the art without undue experimentation within ranges that are not lethal to the plant materials, and provide the best embryo maturation in the case of the Singh seed maturation medium, or the best shoot development in the case of the Singh shoot elongation (C5) medium.

TABLE 2

| Media Components | Singh Seed Maturation | Singh Shoot Elongation (C5) | MS (Commercial) | B5 (Commercial) |
|---|---|---|---|---|
| Media Compositions | | | | |
| Major Salts (10×); 100 ml/L | | | | |
| $KNO_3$ | 30 g/L | 20 g/L | 19 g/L | 30 g/L |
| $(NH_4)_2SO_4$ | 1.34 g/L | — | — | 1.34 g/L |
| $NH_4NO_3$ | 16.5 g/L | 10 g/L | 16.5 g/L | 16.5 g/L |
| $NaH_2PO_4 \cdot H_2O$ | 1.5 g/L | 1 g/L | — | 1.5 g/L |
| $KH_2PO_4$ | 1.7 g/L | 3 g/L | 1.7 g/L | — |
| $MgSO_4 \cdot 7H_2O$ | 3.7 g/L | 3.75 g/L | 3.7 g/L | 5 g/L |
| $CaCl_2 2H_2O$ | 4.4 g/L | 6 g/L | 4.4 g/L | 1.5 g/L |
| Minor Salts I (100×); 10 ml/L | | | | |
| $H_3BO_3$ | 0.3 g/L | 0.3 g/L | 0.62 g/L | 0.3 g/L |
| $MnSO_4 \cdot H_2O$ | 1.0 g/L | 1.0 g/L | — | 1.0 g/L |
| $ZnSO_4 \cdot 7H_2O$ | 0.46 g/L | 0.46 g/L | 0.86 g/L | 0.2 g/L |
| $MnSO_4 \cdot 4H_2O$ | — | — | 2.23 g/L | — |
| Minor Salts II (100×)]; 10 ml/L | | | | |
| KI | 0.042 g/L | 0.042 g/L | 0.083 g/L | 0.075 g/L |
| $CuSO_4 \cdot 5H_2O$ | 0.0013 g/L | 0.0013 g/L | 0.0025 g/L | 0.0025 g/L |
| $Na_2MoO_4 \cdot 2H_2O$ | 0.013 g/L | 0.013 g/L | 0.025 g/L | 0.025 g/L |
| $CoCl_2 \cdot 6H_2O$ | 0.0015 g/L | 0.0015 g/L | 0.0025 g/L | 0.0025 g/L |

TABLE 2-continued

Media Compositions

| Media Components | Singh Seed Maturation | Singh Shoot Elongation (C5) | MS (Commercial) | B5 (Commercial) |
|---|---|---|---|---|
| Iron (10×); 100 ml/L | | | | |
| Na$_2$•EDTA | 0.185 g/L | 0.261 g/L | 0.373 g/L | 0.373 g/L |
| FeSO$_4$•7H$_2$O | 0.139 g/L | 0.249 g/L | 0.278 g/L | 0.278 g/L |
| KOH | — | 0.1503 g/L | — | — |
| Vitamins | | | | |
| Nicotinic acid (500 mg/100 ml) | 2 ml/L | 250 µl/L | 0.5 mg/L | 1 mg/L |
| Pyridoxine HCl (100 mg/100 ml) | 2 ml/L | 1 ml/L | 0.5 mg/L | 1 mg/L |
| Thiamine (100 mg/100 ml) | 1 ml/L | 2.25 ml/L | 0.1 mg/L | 10 mg/L |
| Glycine (100 mg/100 ml) | 2 ml/L | 2 ml/L | 2 mg/L | — |
| Myo-inositol | 0.1 g/L | 0.250 g/L | 0.1 g/L | 0.1 g/L |
| Ascorbic acid | 0.1 g/L | — | — | — |
| L-Glutamine | 292 mg/L | — | — | — |
| Casein hydrolysate | 0.5 g/L | — | — | — |
| Growth Hormones | | | | |
| IAA (10 mg/50 ml) EtOH | 2 ml/L | — | — | — |
| NAA (100 mg/50 ml) EtOH | 2 ml/L | — | — | — |
| Kinetin (50 mg/50 ml) NaOH | 1.30 ml/L | — | — | — |
| BAP (100 mg/100 ml) | 400 µ/L | 1 ml/L | — | — |
| 2,4-D | — | — | — | 2 mg/L |
| Sugars | | | | |
| Sucrose | 40 g/L | 25 g/L | 30 g/L | 20 g/L |
| D-mannitol | 18 g/L | — | — | — |
| Gelrite | 3 g/L | 3 g/L | — | — |
| pH | 5.8 | 5.6 | 5.6 | 5.5 |

As can be seen in Table 2, the MS medium also comprises sugar, present in an amount approximately double the amount present in B5 medium. The sugar can be sucrose, D-mannitol, or sorbitol. Preferably a combination of sucrose and D-mannitol is used wherein there is about twice as much sucrose as D-mannitol. The medium should contain at least about 30 g/L total sugar, or in some embodiments, at least about 40 g/L total sugar, and in other embodiments, at least about 100 g/L total sugar. If too much sugar is used, i.e., more than about 100 g/L, the osmoticum will be unbalanced and the immature seed will die.

Use of too little major salts will prevent or cause slow growth of embryos and use of too much salts will cause embryo death. In a preferred medium, the major salts comprise those of the Murashige and Skoog and Gamborg B5 media. (See Table 2 for comparison.) KNO$_3$ is as present in B5 medium. (NH$_4$)$_2$SO$_4$ is as present in B5 medium; NH$_4$NO$_3$ is as present in MS and B5 medium; NaH$_2$PO$_4$.H$_2$O is as present in B5 medium; MgSO$_4$.7H$_2$O is as present in MS medium; and CaCl$_2$. 2H$_2$O is as present in MS medium. Iron is present in the preferred medium in an amount equal to about one-half the amount used in Murashige and Skoog medium.

The minor salt that has been found to be most important is ZnSO$_4$.7H$_2$O in an amount of about 0.46 g/L. Too much or too little of the minor salts can kill the embryo.

Figure 2:
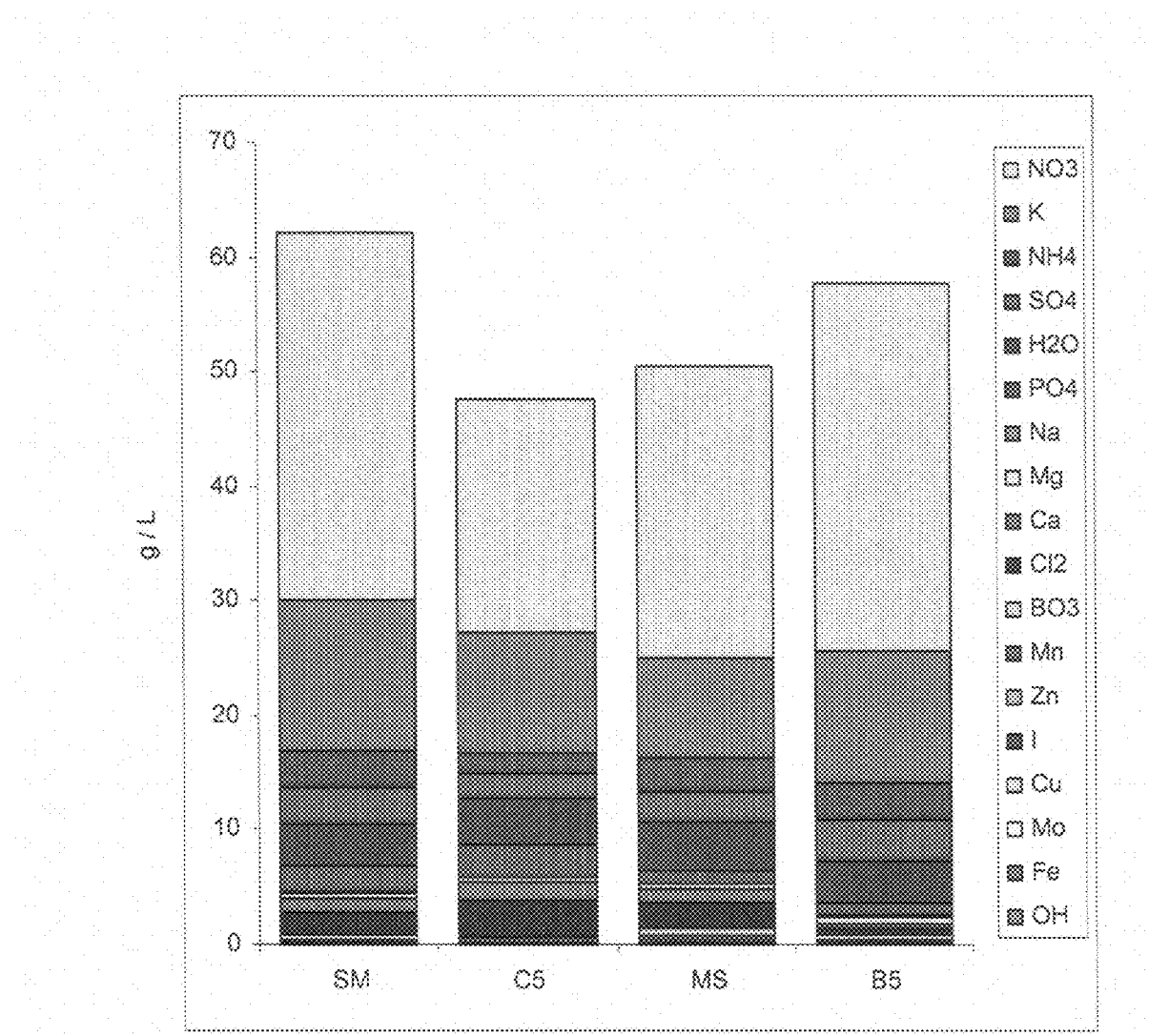
FIG. 2 is a graph showing the ionic concentration of the Singh seed maturation medium and Singh shoot elongation (C5) media of this invention compared with commercial Murashige and Skoog (MS) and Gamborg B5 media.

Table 3 provides a comparison of the percentages of major and minor salts of Singh SM and C5 media with those of commercially available MS and B5 media. Table 4 provides the ionic composition of the ions of the major and minor salts of these media in g/L, as shown graphically in FIG. 2.

TABLE 3

Comparison of percent salts and ions in media

| Component | MW | Ions | % of MW | % SM | % C5 | % MS | % B5 |
|---|---|---|---|---|---|---|---|
| KNO$_3$ | | K | 0.387 | 11.61 | 7.74 | 7.35 | 11.61 |
| | 101.11 | NO$_3$ | 0.613 | 18.39 | 12.26 | 11.647 | 18.39 |
| (NH$_4$)$_2$SO$_4$ | | 2NH$_4$ | 0.214 | 0.287 | 0 | 0 | 0.287 |
| | 122.144 | SO$_4$ | 0.786 | 1.0532 | 0 | 0 | 1.053 |
| (NH$_4$)NO$_3$ | | NH$_4$ | 0.174 | 2.871 | 1.74 | 2.871 | 2.871 |
| | | NO$_3$ | 0.826 | 13.629 | 8.26 | 13.629 | 13.629 |
| NaH$_2$PO$_4$•H$_2$O | | H2O | 0.131 | 0.197 | 0.131 | 0 | 0.197 |
| | | PO$_4$ | 0.688 | 1.032 | 0.688 | 0 | 1.032 |
| | | H$_2$ | 0.015 | 0.023 | 0.015 | 0 | 0.023 |
| | | Na | 0.16 | 0.24 | 0.16 | 0 | 0.24 |
| KH$_2$PO$_4$ | | K | 0.87 | 1.479 | 2.61 | 1.479 | 0 |
| | | H$_2$ | 0.015 | 0.026 | 0.045 | 0.026 | 0 |
| | | PO$_4$ | 0.698 | 1.187 | 2.094 | 1.187 | 0 |

TABLE 3-continued

Comparison of percent salts and ions in media

| Component | MW | Ions | % of MW | % SM | % C5 | % MS | % B5 |
|---|---|---|---|---|---|---|---|
| MgSO$_4$•7H$_2$O | | Mg | 0.099 | 0.366 | 0.371 | 0.366 | 0.495 |
| | | SO$_4$ | 0.39 | 1.443 | 1.463 | 1.443 | 1.95 |
| | | 7H$_2$O | 0.512 | 1.894 | 1.92 | 1.894 | 2.56 |
| CaCl$_2$•2H$_2$O | | Ca | 0.273 | 1.201 | 1.638 | 1.201 | 0.410 |
| | | Cl$_2$ | 0.482 | 2.121 | 2.892 | 2.121 | 0.723 |
| | | 2H$_2$O | 0.245 | 1.078 | 1.47 | 1.078 | 0.368 |
| H$_3$BO$_3$ | | H$_3$ | 0.049 | 0.0147 | 0.015 | 0.030 | 0.015 |
| | 61.834 | BO$_3$ | 0.951 | 0.285 | 0.285 | 0.590 | 0.285 |
| MnSO$_4$•H$_2$O | | Mn | 0.325 | 0.325 | 0.325 | 0 | 0.325 |
| | | SO$_4$ | 0.568 | 0.568 | 0.568 | 0 | 0.568 |
| | | H2O | 0.107 | 0.107 | 0.107 | 0 | 0.107 |
| ZnSO$_4$•7H$_2$O | | Zn | 0.227 | 0.104 | 0.104 | 0.195 | 0.045 |
| | | SO$_4$ | 0.334 | 0.154 | 0.154 | 0.287 | 0.067 |
| | | 7H$_2$O | 0.439 | 0.202 | 0.202 | 0.378 | 0.088 |
| MnSO$_4$•4H$_2$O | | Mn | 0.246 | 0 | 0 | 0.549 | 0 |
| | | SO$_4$ | 0.431 | 0 | 0 | 0.961 | 0 |
| | | 4H$_2$O | 0.323 | 0 | 0 | 0.720 | 0 |
| KI | | K | 0.236 | 0.001 | 0.010 | 0.0196 | 0.018 |
| | | I | 0.764 | 0.032 | 0.032 | 0.063 | 0.057 |
| CuSO$_4$•5H$_2$O | | Cu | 0.255 | 0.0003 | 0.0003 | 0.0006 | 0.0006 |
| | | SO$_4$ | 0.385 | 0.0005 | 0.0005 | 0.001 | 0.001 |
| | | 5H$_2$O | 0.361 | 0.0004 | 0.0005 | 0.001 | 0.0001 |
| Na$_2$MoO$_4$•2H$_2$O | | Na$_2$ | 0.19 | 0.00247 | 0.002 | 0.005 | 0.005 |
| | 241.962 | Mo | 0.397 | 0.005 | 0.005 | 0.010 | 0.010 |
| | | O$_4$ | 0.265 | 0.003 | 0.003 | 0.007 | 0.007 |
| | | 2H$_2$O | 0.149 | 0.002 | 0.002 | 0.004 | 0.004 |
| CoCl$_2$•6H$_2$O | | Co | 0.248 | 0.0004 | 0.0004 | 0.0006 | 0.0006 |
| | | Cl$_2$ | 0.298 | 0.0004 | 0.0004 | 0.0007 | 0.0007 |
| | | 6H$_2$O | 0.454 | 0.001 | 0.001 | 0.001 | 0.001 |
| Na$_2$•EDTA | | Na$_2$ | 0.124 | 0.023 | 0.0324 | 0.0463 | 0.046 |
| | 372.2 | EDTA | 0.876 | 0.162 | 0.229 | 0.327 | 0.327 |
| FeSO$_4$•7H$_2$O | | Fe | 0.201 | 0.028 | 0.050 | 0.056 | 0.056 |
| | 278.023 | SO$_4$ | 0.346 | 0.0481 | 0.086 | 0.096 | 0.096 |
| | | 7H$_2$O | 0.454 | 0.0637 | 0.113 | 0.126 | 0.126 |
| KOH | | K | 0.697 | 0 | 0.105 | 0 | 0 |
| | 56.108 | OH | 0.303 | 0 | 0.046 | 0 | 0 |

TABLE 4

Comparison of ionic concentrations (g/L) of media

| Ion | SM g/L | C5 g/L | MS g/L | B5 g/L |
|---|---|---|---|---|
| OH | 0 | 0.04554 | 0 | 0 |
| Fe | 0.0279 | 0.0500 | 0.0559 | 0.0559 |
| Mo | 0.0052 | 0.0052 | 0.0099 | 0.0099 |
| Cu | 0.0003 | 0.0003 | 0.0006 | 0.0006 |
| I | 0.0321 | 0.03209 | 0.0634 | 0.0573 |
| Zn | 0.1044 | 0.1044 | 0.1952 | 0.0454 |
| Mn | 0.325 | 0.325 | 0.5486 | 0.325 |
| BO$_3$ | 0.2853 | 0.2853 | 0.5896 | 0.2853 |
| Cl$_2$ | 2.1212 | 2.8924 | 2.1215 | 0.7237 |
| Ca | 1.2012 | 1.638 | 1.2012 | 0.4095 |
| Mg | 0.3663 | 0.3713 | 0.3663 | 0.495 |
| Na | 0.2654 | 0.1948 | 0.0510 | 0.2910 |
| PO$_4$ | 2.2186 | 2.782 | 1.1866 | 1.032 |
| H$_2$O | 3.5440 | 3.9461 | 4.2022 | 3.4508 |
| SO$_4$ | 3.2665 | 2.2708 | 2.7885 | 3.7352 |
| NH$_4$ | 3.1578 | 1.74 | 2.871 | 3.1578 |
| K | 13.0989 | 10.4647 | 8.8486 | 11.6277 |
| NO$_3$ | 32.019 | 20.52 | 25.276 | 32.019 |

The vitamins that have been found to be most important are ascorbic acid, L-glutamine, and casein hydrolysate in the amounts set forth in Table 2. Embryos will not mature rapidly when too little of these vitamins are used, and will die if too much of the vitamins are used.

In a preferred medium for culture of the seeds to produce callus, the vitamins comprise those of Murashige and Skoog medium and in addition comprise ascorbic acid, L-glutamine and casein hydrolysate.

The Singh C5 medium used for multiple shoot regeneration is also a novel aspect of this invention. The preferred multiple shoot regeneration medium contains BAP as the only growth hormone. BAP is a cytolinin required for shoot initiation. Without BAP, shoots will not be formed. The use of 2,4-D as the only growth hormone produced only friable, large and nonregenerable calluses. Using BAP, the inventor did not see chromosomal aberrations such as changes in ploidy or breakage.

The hybrid plants can be screened for desirable agronomic traits or genes inherited from the wild parent, and those carrying the traits selected for further breeding. Screening for resistance to SBR, SCN, soybean aphid, BPMV, and other traits found in wild soybean are known to the art or readily devised without undue experimentation by those skilled in the art. Genes contributing to these resistance traits for which sequence is known may be identified by means known to the art such as genomic in situ hybridization (GISH) and molecular markers.

This invention also provides a method for producing and identifying at least one amphidiploid plant from a hybrid between a first parent plant of a wild perennial *Glycine* species and a second parent plant that is a domestic annual *Glycine* cultivar, wherein the amphidiploid plant is capable of backcrossing with a plant that is a domestic annual *Glycine* cultivar to produce progeny. The method comprises: (a) providing multiple plants that are hybrids between a first parent plant of a wild perennial *Glycine* species and a second parent plant that is a domestic annual *Glycine* cultivar; (b) selecting from these hybrid plants ones that contain half the number of chromosomes present in the first parent plant and half the number of chromosomes present in the second parent plant; (c) sterilizing the selected plants to destroy microorganisms present thereon; (d) soaking roots and shoots of the sterilized plants in sterilized colchicine for four to eight hours in light in an incubator; (e) transferring the plants to soil; (f) counting the number of chromosomes in root tips of said plants, e.g., counting chromosomes present in root tip cells; (g) and selecting at least one plant that has double the number of chromosomes as were present in the original hybrid plants, e.g., the number of chromosomes that were present in actively-growing roots about 2-3 mm in length, and anthers of the original hybrid plants; thereby producing and identifying at least one amphidiploid plant that is capable of backcrossing with a plant that is a domestic annual *Glycine* cultivar to produce progeny.

The amphidiploid plants are partially female-fertile and generally male-sterile, but occasionally can produced selfed pods. Thus, the plants selected as amphidiploid plants can be observed and those that bear selfed pods can be identified. Seeds from such pods can be grown by the method described above for culturing embryos of the $F_1$ hybrid plants. The amphidiploid plants can also be vegetatively reproduced. Thus, this invention also provides an amphidiploid plant grown from selfed seed of an amphidiploid plant produced by colchicine treatment, or a vegetatively-reproduced amphidiploid plant produced by colchicine treatment; and progeny or plant tissue of said amphidiploid plants. Such reproduced amphidiploid plants can be screened to determine the presence of a desirable agronomic trait inherited from the wild perennial ancestor. Plant tissue is defined herein to include seeds as well as roots, shoots, leaves and all other components of a plant.

In embodiments of this invention, the amphidiploid plant has a gene for a desirable agronomic trait inherited from the wild perennial *Glycine* species.

This invention also provides methods for backcrossing amphidiploid plants made from wild/domestic soybean hybrids into domestic soybean. Each backcross generation can be screened for the presence of a desirable agronomic trait or gene derived from the wild perennial ancestor and those having the trait or gene selected for further backcrossing. The backcrossing method comprises: (a) providing a plurality of amphidiploid plants made from at least one hybrid between a first parent plant of a wild perennial *Glycine* species and a second parent plant that is a domestic annual *Glycine* cultivar, wherein the amphidiploid plants are capable of backcrossing with a plant that is a domestic annual *Glycine* cultivar to produce progeny, and wherein the amphidiploid plants have at least one gene for a desirable agronomic trait inherited from the wild perennial *Glycine* parent plant; (b) providing a plurality plants of a domestic soybean variety; (c) allowing the amphidiploid plants to produce flowers; (d) allowing the domestic soybean plants to produce flowers; (e) emasculating flowers of the amphidiploid plants; (f) fertilizing the flowers of the amphidiploid plants with pollen from the domestic soybean plants; (g) obtaining at least one immature seed from a pod resulting from the fertilized flowers; (h) culturing the seed on a seed maturation medium to produce shoots; (i) rooting the shoots to form plantlets, and hardening the plantlets to form $BC_1$ plants; and (j) counting the number of chromosomes in the $BC_1$ plants and selecting those that have 40 paired chromosomes and half the number of unpaired chromosomes as were present in the original wild perennial *Glycine* species; thereby producing a $BC_1$ plant having a gene for a desirable agronomic trait inherited from a wild perennial *Glycine* species.

The backcross generation is screened for the presence of the desired trait or gene inherited from the wild ancestor, and those having the trait or gene are selected for breeding. The method is repeated to produce further backcross generations.

Although the first production of $BC_3$-$BC_6$ generations by the methods of this invention is approximately a ten-year project, the time can be cut down to about four or five years thereafter. Thus, by the foregoing methods, desired domestic soybean varieties carrying and expressing genes for desirable agronomic traits derived from wild soybean ancestors, and without wild soybean DNA that produces undesirable effects, can be produced after three to six backcross generations in a period from initiation of hybridization to production of the desired backcrossed plant carrying the gene, of about three to four years, depending on the number of generations and manpower required to eliminate unwanted wild soybean chromosomes. The methods of this invention can be reproduced by skilled workers exercising a high degree of patience and care.

In embodiments of this invention, the methods and media used above are used to produce the $BC_1$ and $BC_2$ generations, and may or may not be required for further backcross generations. When backcross generations start producing enough viable seeds (i.e., seeds that can be grown into plants without resort to tissue culture for production of multiple embryos and shoot generation) to provide sufficient numbers of plants for further breeding, the plants may be grown out from seeds. In general backcross plants having more than three chromosomes derived from the wild perennial *Glycine* ancestor will not produce seed that can be grown without resort to tissue culture.

Thus, this invention provides backcrossed plants, progeny and tissue produced by the above methods.

The $BC_2$ and $BC_3$ and subsequent backcross generations will contain fewer wild soybean chromosomes than their immediate parents. In addition to testing to select plants of these generations that retain desirable traits or genes, the chromosomes can be counted, and those having only one wild chromosome selected for use in determining desirable genes located on that chromosome.

In one embodiment, this method is a method for selecting a desired backcrossed plant that is descended from a hybrid between a wild perennial *Glycine* ancestor and a domestic soybean variety ancestor wherein the backcrossed plant has been successively backcrossed with at least three domestic soybean variety ancestors (which may be the same or different varieties) and wherein the plant has only one chromosome inherited from said wild perennial *Glycine* ancestor. This method comprises: (a) producing a backcrossed plant that is descended from a hybrid between a wild perennial *Glycine* ancestor and a domestic soybean variety ancestor that has been successively backcrossed with three domestic soybean variety ancestors; (b) counting the chromosomes of the backcrossed plant, and if it has 40 paired chromosomes inherited from domestic soybean and only one chromosome inherited from said wild perennial *Glycine* ancestor, selecting it as the desired plant; or (c) if the plant has two or three chromosomes inherited from the wild perennial *Glycine* ancestor, selfing it and selecting progeny plants having 40 paired chromosomes inherited from domestic soybean and only one chromosome inherited from the wild perennial *Glycine* ancestor; or (d) if the plant has more than three chromosomes inherited from the wild perennial *Glycine* ancestor, again backcrossing it with a plant of a domestic soybean variety and counting the chromosomes of the resulting further backcrossed plant; and (e) continuing backcrossing the resulting plant from each backcross with a plant of a domestic soybean variety and counting the chromosomes of each resulting plant until a resulting plant is identified that has only one chromosome inherited from the wild perennial *Glycine* ancestor.

This invention therefore provides plants produced by above method of as well as progeny or plant tissue thereof.

In addition, the invention provides a method for making a plurality of plants, each having a different single chromosome inherited from its wild perennial *Glycine* ancestor. The method comprises identifying the single chromosome inherited from the wild perennial *Glycine* ancestor present in each plant producing further backcross generations until a plurality of plants with different single chromosomes inherited from the wild perennial *Glycine* ancestor has been produced. In an embodiment of this invention, backcrossing is continued until plants containing no more than three chromosomes from the wild perennial *Glycine* ancestor are produced. The method includes producing a plurality of such plants that collectively contain all the chromosomes present in the hybrid between the wild perennial *Glycine* ancestor and the domestic soybean ancestral to the plants in the set. Single plants as well as the complete set of plants containing all the wild chromosomes are provided by this invention, as well as progeny and plant tissue thereof.

Seeds of plants having one to three chromosomes inherited from their wild ancestors can be treated to cause recombination of a chromosome inherited from said wild perennial *Glycine* ancestor with a chromosome inherited from said domestic soybean variety ancestor. The treated plant can be backcrossed with domestic soybean and tested for the presence of the desired traits or genes and counting its chromosomes, and if it carries the desired traits or genes and has no wild soybean chromosomes, it can be selected for further breeding.

Preferably, it is bred with a domestic soybean cultivar that has desirable agronomic traits (referred to herein as an "elite" soybean line). The resultant plants can then be further tested so that those having all the desirable agronomic traits derived from both parents can be selected for further breeding or use in crops. Desirable traits of elite soybean lines are known to the art, and include traits selected from the group consisting of desirable yield, lodging, plant height, field emergence, resistance or tolerance to herbicides, bacteria, fungi, viruses and nematodes; tolerance to drought, heat, chilling, freezing, excessive moisture, salt stress, oxidative stress; increased yields; food content and makeup; physical appearance; male sterility; drydown; standability; prolificacy; sugar properties; oil quantity and quality, protein quantity and quality, and fatty acids.

EXAMPLES

Example 1

Pollination

Wide crosses were made using domestic soybean varieties Dwight (Accession No. PI 597386), Macon (Accession No. PI593258), and Ina (Accession No. PI606749), and wild perennial *G. tomentella* (Accession Nos. PI441001 and PI441008). The soybean varieties all have 40 chromosomes (2n=40) and $G_1G_1$ genomes. *G. tomentella* PI441001 and PI441008 both have 78 chromosomes (2n=78) and $D_3D_3EE$) genomes.

Both *G. tomentella* accessions are highly resistant to soybean rust (Schoen, et al. (1992), "Resistance of *Glycine tomentella* to soybean leaf rust *Phakospora pachyrhizi* in relation to ploidy level and geographic distribution," Theor. Appl. Genet. 83:827-832, R. L. Nelson personal communication), and soybean cyst nematode (Riggs et al. (1998), "Possible transfer of resistance to *Heterodera Glycines* from *Glycine tomentella* to *Glycine max*.," J. Nematol. (Suppl.) 30(4S):547-552).

When domestic soybean was used as the female parent, soybean flower buds prior to anthesis were emasculated by removing the calyx and corolla of the flower, and then removing the anthers with a fine forceps, taking care not to injure the gynoecium. Pollen from freshly-opened flowers of *G. tomentella* (2n=78) was obtained by removing the wing, making a slit in the keel, and very carefully removing the gynoecium along with the attached anthers and dusting the pollen onto the emasculated soybean flower, taking care not to shake the anthers from the gynoecium to which they are attached. As much pollen as possible was applied. No hormone treatment was applied to the pollinated flowers on the day of pollination, so as not to cause loss of pollen grains from the soybean stigmas. (In cases where domestic soybean was used as the male parent, the process was reversed, i.e., the *G. tomentella* flower buds were emasculated and pollen from the domestic soybean flowers was applied.

Example 2

Pod Set

Beginning twenty-four hours after pollination, and every day for 19-21 days, in the mornings, the pollinated soybean gynoecia and subsequent developing pods were sprayed with a growth hormone mixture that had been allowed to come to room temperature. The hormone mixture consisted of gibberellic acid (GA3), naphthaleneacetic acid (NAA) and kinetin (K), using 100 mg GA3, 25 mg NAA and 5 mg K per liter of solution. (Jena, K. K. and Khush, G. S. (1989), "Monosomic alien addition lines of rice: production, morphology, cytology, and breeding behavior," Genome 32:449-455). Gibberellic acid alone was not effective. A glove was used to protect the skin from the chemicals. After 19-21 days, the pods were physically removed from the plants. One function of the spray is to keep the abscission layer attaching the pod to the plant from drying out and causing the pod to drop off. The hybrid seeds were yellow-green and suspended in dark-green pods, and could easily be distinguished from selfed soybean pods that occasionally developed. There were one or two seeds per hybrid pod. Occasionally, the hybrid pods developed without seed. In earlier experiments without growth hormone spray, pod set was extremely low. Extreme care was used during this period to avoid damaging the tissue while applying the growth hormone. Even so, only about 1% of the pollinated flowers produced pods. In experiments in which the hormone spray treatment was kept up longer than about 21 days, endosperm started to develop, which killed the embryos, and after 25-26 days of hormone spray treatment, instead of being yellow-green, the hybrid seeds were brownish.

Example 3

Surface Sterilization

After removing the pods from the plants, the pods were surface-sterilized in a solution of 50% commercial Clorox (50 ml commercial Clorox plus 50 ml distilled water) for 15 to 20 minutes in a sterile laminar flow hood. The pods were stirred every five minutes to make sure the entire pod was sterilized, and then removed from the Clorox solution and washed two times in distilled sterile water that has been autoclaved to remove all the Clorox. With a very fine sterilized tweezers and sterilized scalpel, the pod was dissected under a dissecting microscope to remove the yellow-green watery seed.

Example 4

Embryo Maturation

Immediately after dissecting and removing the seeds from the hybrid pods, they were embedded in a seed maturation (SM) medium of this invention. The medium composition is set forth in Table 2, which provides a comparison of the SM medium of this invention with B5 medium (Gamborg, O. L. et al. (1968), Exp. Cell Res. 151-8) and Murashige and Skoog medium (Murashige T. and Skoog F. (1962), "A revised medium for rapid growth and bioassays with tobacco tissue cultures," Physiol. Plant 18:100-127).

The seeds were kept in Petri plates on the SM medium with thirteen hours of low-intensity light at 25° C. The incubators were checked twice a day to ensure proper conditions were being maintained. The seeds and subsequently-developed calluses were transferred to fresh medium every two to three weeks. If the material was observed to be beginning to turn dark, it was immediately placed on fresh medium. The endosperm did not develop because the seeds were not attached to a plant. In earlier experiments, attempts to put hybrid embryos dissected from the immature seed directly onto the SM medium were unsuccessful, as the embryos all died due to shock. Moreover, because of the low percentage of success in subsequent steps of production of fertile hybrid plants and backcrosses with soybean lines, it was desired to produce as many embryos as possible from each seed. Therefore, growth hormones were used in the SM medium to prevent seed germination and development of a single embryo. Rather the medium was designed to produce callus, which in turn produced multiple embryos from each seed. After about three months, the seed turns black and the embryo turns yellow-green and callus material spools out from the seed case. The callus is transferred to fresh C5 medium every two weeks until it starts to bud, i.e., until somatic embryos begin to form.

Example 5

Multiple Shoot Regeneration

Young embryos were dissected from the callus tissue, and brown callus tissue was discarded. The embryos were very carefully transferred to the multiple shoot regeneration medium designated as C5 in Table 2. Within one to two months, multiple shoots initiated. Individual embryos that formed on this medium were dissected out and transferred to fresh C5 medium. More than 500 small embryos were obtained from one hybrid seed, and can be kept on this medium for several years as long as they are transferred to fresh C5 medium every 2 to 3 weeks. New embryos continue to form on this medium and may produce shoots that die or produce roots.

Example 6

Rooting

Actively growing shoots were removed one at a time, and each was placed on a rooting medium made up in distilled water containing 2.2 g/L of one-half strength MS salts and vitamins (Phytotechnology; Lot #05G51916C) plus 10 g/L sugar and 1.5 g/L gelrite. No growth hormones were used in this medium. The gelrite was dissolved in a microwave for one minute, three times before autoclaving. Containers with shoots were kept in an incubator in sterile conditions. Rooting initiated within a week. Approximately 50 percent of the shoots formed healthy roots and elongated shoots.

Example 7

Acclimatization

Shoots with well-developed roots and shoots were transferred into pots containing soil that had been pre-fertilized with one-half strength Hoagland solution and taken to the greenhouse. The pots were covered with a clear plastic bag and kept in the shade to prevent desiccation. After three to four days, the plastic bag was halfway removed, and completely removed after six to eight days. The seedlings began to grow within a week. The process from initiation of hybridization to having five hybrid plants growing in the greenhouse took nine to twelve months.

Example 8

Confirmation of Hybrid Nature of Plants

The hybrid plants were checked to determine their chromosome numbers. When the original G. tomentella parents had 78 chromosomes (2n=78), since the soybean parents had 40 chromosomes (2n=40), the hybrids were expected to have 59 unpaired chromosomes at meiotic metaphase I: 39 from the G. tomentella parent and 20 from the soybean parent. This was confirmed. The somatic metaphase 59 chromosomes present in the hybrid plants contained, as expected, two nucleolus organizer chromosomes (NOR), one from each parent. (When the original G. tomentella parents had 80 chromosomes (2n=80), the hybrids were expected to have 60 unpaired chromosomes including three nucleolus organizer chromosomes (80-chromosome G. tomentella has four NOR and soybean has two NOR). The plants were male- and female-sterile due to the inability of their chromosomes to pair.

The following hybrids were produced by the above methods:

G. max. cv. Dwight (2n=40, genome $G_1G_1$)×G. tomentella (2n=78, genome $D_3D_3EE$) PI 441001. (2) G. tomentella (2n=78, genome $D_3D_3EE$) PI 441001×G. max. cv. Dwight (2n=40, genome $G_1G_1$). (3) G. max. cv. Ina (2n=40, genome $G_1G_1$)×G. tomentella (2n=78, genome $D_3D_3EE$) PI 441001. (4) G. max. cv. Macon (2n=40, genome $G_1G_1$)×G. tomentella (2n=78, genome $D_3D_3EE$) PI 441001. (5) G. max. cv. Dwight (2n=40, genome $G_1G_1$)×G. tomentella (2n=78, genome $D_3D_3EE$) PI 441008. (6) G. max. cv. Dwight (2n=40, genome $G_1G_1$)×G. tomentella (2n=78, genome $D_3D_3EE$) PI 505258. (8) G. max. cv. Dwight (2n=40, genome $G_1G_1$)×G. tomentella (2n=78, genome $D_3D_3EE$) PI 563892. (9) G. max. cv. Dwight (2n=40, genome $G_1G_1$)×G. tomentella (2n=78, genome $D_3D_3EE$) PI 583892. The parent first mentioned in the crosses described above is the female parent.

Cross (2) above carries cytoplasm of *G. tomentella*. This cross was made to diversify the cytoplasm of soybean with the aim of obtaining cytoplasmic male sterility, a prerequisite for producing hybrid soybean.

Crosses (1)-(4) have been identified based on morphological traits, chromosome count and single sequence repeat (SSR) markers. All contained the expected 2n=59 chromosomes.

Example 9

Production of Amphidiploid Plants

Repeated attempts to double the chromosome number of the hybrid plants to produce amphidiploid plants that would be fertile using colchicine by the method of Cheng and Hadley (Cheng, H. H., and Hadley, H. H. (1983), "Studies in polyploid in soybeans: A simple and effective colchicine technique of chromosome doubling for soybean (*Glycine max* (L.) Merr.) and its wild relatives," Soybean Genet. Newsl. 10:23-24), were failures. Also a method used successfully to produce amphidiploid plants from a similar wide hybrid between *G. tomentella* and *G. max* cv. Altona involving grafting plant material from the hybrid plants comprising nodes onto soybean and treating with colchicine failed repeatedly. Therefore the following method, which was successful in repeated trials, was developed:

Fifty sterilized plantlets were submerged (shoot and root) in 0.2% filter-sterilized colchicine for four to eight hours at 25° C. in light in an incubator. The plantlets were washed in running cold water from the tap for one hour, and transferred to pots in the greenhouse and acclimatized as set forth above. Plantlet mortality was about 75%. After two to three weeks, plantlets began showing signs of life, although appearing somewhat sick, and shoots with leathery, large and hairy leaves established slowly. Flowers were larger than $F_1$ and parent flowers.

The chromosome number was checked for each plant at meiosis, showing plants containing 59 pairs of chromosomes (known as bivalents).

The plants were observed at least twice a day to determine if pods had been produced. Cleistogamous flowers were noted as an indication that selfed pods might appear. When pods were identified, they were tagged so that they could be found again. Pod set is very rare in the amphidiploid plants, but occasionally pods with one seed were found. Fifteen seeds were harvested, and are being stored in long-term storage. These seeds are larger than those of wild soybean and smaller than those of domestic soybean.

The amphidiploid plants were vegetatively reproduced from cuttings.

Example 10

Production of Backcrossed Generation ($BC_1$) Plants

Flowers from the amphidiploid plants were emasculated as described above, and pollinated with pollen obtained from flowers of the *G. max* cv. Dwight domestic soybean plants as described above. The plants were checked twice a day and any pods observed were tagged.

After 19 to 21 days, fifty seeds were removed and cultured. The embryo from one seed callused and became morphogenic. More than 500 shoots were obtained from this seed and grown in culture, and 15 plants have been rooted and transferred to the greenhouse. They produce pods with one or two seeds after pollination with Dwight soybean.

Chromosomes were checked. The $BC_1$ plants had 79 chromosomes, 40 from soybean and 39 from *G. tomentella*. The soybean chromosomes paired while the *G. tomentella* chromosomes moved randomly toward the poles. The genome was $G_1G_1D_3E$ as expected.

It took three years from when the first hybridizations were begun to produce the $BC_1$ generation. $BC_1$ plants can be vegetatively reproduced as required. Occasionally they can be selfed.

Example 12

Production of Second Backcrossed Generation ($BC_2$) Plants $BC_1$ plants as described above were backcrossed with *G. max* cv. Dwight, again using the domestic soybean Dwight as the male parent. Seeds are cultured as described above, and a $BC_2$ generation of plants is produced. The procedure produces about three pods per 1000 pollinations.

With this generation, chromosomes from the wild parent begin to be eliminated). The $BC_2$ plants have 40 paired chromosomes from the domestic soybean parent and 10 to 20 from the *G. tomentella* parent that are not paired. The genome for the $BC_2$ plants is also variable, comprising $G_1G_1$ from the domestic soybean parent and $D_3$ and/or E from the wild parent. Plants from the $BC_2$ generation are tested for the presence of desirable traits from *G. tomentella*, and those possessing the traits are selected for further backcrossing.

Example 13

Production of Third Through Sixth Generation Backcrossed ($BC_3$-$BC_6$) Plants $BC_2$ plants as described above are backcrossed with *G. max* cv. Dwight, again using the domestic soybean Dwight as the male parent to produce a $BC_3$ generation. The seeds may be cultured as above, but if the resultant plant contains 42 chromosomes or less, culturing is not necessary. The procedure is repeated, backcrossing the $BC_3$ generation to Dwight to produce a $BC_4$ generation, further backcrossing this generation to Dwight to produce a $BC_5$ generation, and then backcrossing the $BC_5$ generation to Dwight to produce a $BC_6$ generation.

Further elimination of *G. tomentella* chromosomes occurs in the $BC_3$-$BC_6$ plants. They contain 40 paired soybean chromosomes and a variable number of unpaired *G. tomentella* chromosomes. Some $BC_3$-$BC_6$ plants with 2n=41 chromosomes are male sterile, and they are backcrossed to Dwight soybean in order to maintain the line.

$BC_3$-$BC_6$ plants having the desired traits can be further backcrossed to elite soybean lines having desirable traits to yield new soybean varieties or hybrids useful for crop production.

$BC_3$-$BC_6$ plants with 2n=41 chromosomes are cytologically identified as containing 40 soybean chromosomes and one *G. tomentella* chromosome. These plants are screened for traits such as SBR, SCN, aphid resistance and BPMV derived from the wild *tomentella* parent, thereby identifying which *G. tomentella* chromosome or chromosomes carry the trait. Plants with 41 to 44 chromosomes having desired traits are irradiated to induce translocation of the traits from the *G. tomentella* chromosome to a *G. max* chromosome, in case desired traits are not transferred to domestic soybean from *G. tomentella* by homoeologous chromosome pairing, and the resultant plants screened for the desired traits and for lack of extraneous *G. tomentella* DNA, and used for further backcrossing to produce varieties or hybrids suitable for crop production.

The invention claimed is:

1. A method for producing at least one hybrid between a first parent plant of a wild perennial *Glycine* species, which carries a desirable agronomic trait, and a second parent plant that is a domestic annual *Glycine* cultivar, wherein said hybrid carries said desirable agronomic trait and is capable of being backcrossed with a domestic annual *Glycine* cultivar to produce at least one plant of a first backcross (BC1) generation that retains said desirable trait wherein a desired backcrossed plant carrying said desirable agronomic trait is produced within a time period of about three to four years, said method comprising:
   (a) providing a plurality of first and second parent plants;
   (b) allowing the parent plants to flower;
   (c) emasculating flowers of one of said first or second parent plants and fertilizing said emasculated flowers with pollen from the other of said first or second parent plants;
   (d) obtaining at least one immature seed from a pod resulting from said fertilized flowers;
   (e) culturing said seed on a seed maturation medium comprising sufficient growth hormones to produce morphogenic callus wherein said medium prevents seed germination;
   (f) culturing embryos produced by said callus on a multiple shoot-regeneration medium to produce shoots;
   (g) rooting said shoots to form plantlets, and hardening said plantlets to form hybrid plants; and
   (h) treating hybrid plants of step (g) with colchicine to double their chromosome number, thereby making at least amphidiploid plant that is capable of being backcrossed with a domestic annual *Glycine* cultivar to produce at least one plant of a $BC_1$ generation carrying said desirable agronomic trait.

2. The method of claim 1 wherein said wild perennial *Glycine* species is selected from the group consisting of *G. canescens, G. argyrea, G. clandestina, G. latrobeana, G. albicans, G. aphyonota, G. arenaria, G. curvata, G. cyrtoloba, G. dolichocarpa, G. falcata, G. gracei, G. hirticaulis, G. lactovirens, G. latifolia, G. microphylla, G. montis-douglas, G. peratosa, G. pescadrensis, G. pindanica, G. pullenii, G. rubiginosa, G. stenophita, G. syndetika G. tabacina* and *G. tomentella*.

3. The method of claim 1 wherein said wild perennial *Glycine* species has a genome selected from the group consisting of A, D and E genomes, and combinations thereof.

4. The method of claim 1 also comprising:
   (i) backcrossing at least one amphidiploid plants of step (h) with a domestic annual *Glycine* cultivar, thereby producing plants of a $BC_1$ generation; and
   (j) identifying at least one plant of said $BC_{-1}$ generation, or progeny thereof, that retains said desirable agronomic trait.

5. The method of claim 1 wherein said desirable agronomic trait is selected from the group consisting of soybean nematode resistance, soybean rust resistance, bean pod mottle virus resistance and aphid resistance.

6. The method of claim 1 wherein said wild perennial *Glycine* species is *G. tomentella*.

7. The method of claim 1 wherein said seed maturation medium comprises a growth hormone selected from the group consisting of indole acetic acid (IAA), 1-naphthalene acetic acid (NAA), benzylaminopurine (BAP), kinetin and combinations of any of the foregoing.

8. The method of claim 7 wherein said seed maturation medium also comprises more than 30 g/L sugar.

9. The method of claim 8 wherein said sugar comprises 18 g/L D-mannitol.

10. The method of claim 1 wherein said multiple shoot regeneration medium contains BAP as the only growth hormone.

11. The method of claim 1 wherein the wild perennial parents are the female parents.

12. The method of claim 1 wherein the wild perennial parents are the male parents.

13. The method of claim 1 wherein step (h) is performed by:
   (i) providing multiple hybrid plants of step (g);
   (ii) selecting from said hybrid plants ones that contain half the number of chromosomes present in the first parent plant and half the number of chromosomes present in the second parent plant;
   (iii) sterilizing said plants to destroy microorganisms present thereon;
   (iv) soaking roots and shoots of said plants in sterilized colchicine for four to eight hours in light in an incubator.
   (v) transferring said plants to soil;
   (vi) examining the number of chromosomes present in said plants; and
   (vii) selecting at least one plant that has double the number of chromosomes as were present in the original hybrid plants of step (i).

14. The method of claim 13 wherein said wild perennial *Glycine* species is selected from the group consisting of *G. canescens, G. argyrea, G. clandestina, G. latrobeana, G. albicans, G. aphyonota, G. arenaria, G. curvata, G. cyrtoloba, G. dolichocarpa, G. falcata, G. gracei, G. hirticaulis, G. lactovirens, G. latifolia, G. microphylla, G. montis-douglas, G. peratosa, G. pescadrensis, G. pindanica, G. pullenii, G. rubiginosa, G. stenophita, G. syndetika* and *G. tabacina.* and *G. tomentella* (2n=38; 40, 78, and 80).

15. The method of claim 13 wherein said wild perennial *Glycine* species has a genome selected from the group consisting of A, D and E genomes, and combinations thereof.

16. The method of claim 13 wherein said amphidiploid plant has a gene for a desirable agronomic trait inherited from said wild perennial *Glycine* species.

17. The method of claim 13 wherein said desirable agronomic trait is selected from the group consisting of soybean nematode resistance, soybean rust resistance, bean pod mottle virus resistance and aphid resistance.

18. The method of claim 13 wherein said wild perennial *Glycine* species is *G. tomentella*.

19. The method of claim 13 also comprising selfing or vegetatively reproducing said amphidiploid plant.

20. The method of claim 4 wherein step (i) is performed by:
   (i) providing a plurality of amphidiploid plants of step (h);
   (ii) providing a plurality plants of a domestic soybean variety;
   (iii) allowing the amphidiploid plants to produce flowers;
   (iv) allowing the domestic soybean plants to produce flowers;
   (v) emasculating flowers of the amphidiploid plants;
   (vi) fertilizing the flowers of the amphidiploid plants with pollen from the domestic soybean plants;
   (vii) obtaining at least one immature seed from a pod resulting from the fertilized flowers;
   (viii) culturing the seed on a seed maturation medium to produce shoots;
   (ix) rooting the shoots to form plantlets, and hardening the plantlets to form $BC_1$ plants; and (x) counting the number of chromosomes in the $BC_1$ plants and selecting those that have 40 paired chromosomes and half the number of unpaired chromosomes as were present in the original wild perennial *Glycine* species;

thereby producing a $BC_1$ plant carrying the desirable agronomic trait inherited from the wild perennial *Glycine* species.

21. The method of claim 20 wherein said immature seed is cultured on a seed maturation medium comprising growth hormones to mature embryos which produce morphogenenic callus, said morphogenic embryos subsequently producing shoots.

22. The method of claim 21 wherein said desirable agronomic trait is selected from the group consisting of soybean nematode resistance, soybean rust resistance, bean pod mottle virus resistance and aphid resistance.

23. The method of claim 4 also comprising producing at least one backcross $BC_2$ plant which is a cross between a $BC_1$ plant of step (j) and a parent plant of a domestic soybean variety, wherein said $BC_2$ plant carries the desirable agronomic trait inherited from the wild perennial soybean species, said method further comprising:
(k) providing at least one of said $BC_1$ plants and at least one of said parent plants of a domestic soybean variety;
(l) allowing said $BC_1$ plant to produce flowers;
(m) fertilizing flowers of said $BC_1$ parent plants of step (k) with pollen from said domestic parent plants of step (k);
(n) obtaining at least one immature seed from a pod resulting from said fertilized flowers of step (n);
(o) culturing said seed of step (n) on a seed maturation medium to produce shoots;
(p) rooting said shoots of step (o) to form plantlets, and hardening said plantlets to form $BC_2$ plants; and
(q) testing the $BC_2$ plants for the presence of a gene for the desirable agronomic trait inherited from the wild perennial *Glycine* species and selecting those plants that carry said trait;
thereby producing at least one $BC_2$ plant carrying the desirable agronomic trait inherited from the wild perennial *Glycine* species.

24. The method of claim 23 wherein in step (o) said immature seed is cultured on a seed maturation medium comprising growth hormones to form callus, wherein said callus is capable of producing embryos from which whole plants can be generated.

25. The method of claim 23 wherein said desirable agronomic trait is selected from the group consisting of soybean nematode resistance, soybean rust resistance, bean pod mottle virus resistance and aphid resistance.

26. The method of claim 23 further comprising providing a plurality of said $BC_2$ plants having said trait, counting the number of chromosomes in said $BC_2$ plants and selecting those that have 40 paired chromosomes and less than half the number of unpaired chromosomes as were present in the original wild perennial *Glycine* species, and testing the selected $BC_2$ plants for the presence of the desirable agronomic trait inherited from the wild perennial *Glycine* species to identify at least one $BC_2$ that carries said trait.

27. The method of claim 23 also comprising producing at least one third backcross $BC_3$ plant which is a cross between said $BC_2$ plant and a parent plant of a domestic soybean variety, wherein said $BC_2$ plant carries the desirable agronomic trait inherited from the wild perennial soybean species, said method further comprising:
(r) providing at least one said $BC_2$ parent plant and at least one parent plant of a domestic soybean variety;
(s) allowing said parent plants to produce flowers;
(t) fertilizing flowers of said $BC_2$ parent plants with pollen from said domestic parent plants;
(u) obtaining seeds from pods resulting from said fertilized flowers;
(v) growing plants from the seeds of step (u) to produce $BC_3$ plants; and
(w) testing the $BC_3$ plants for the presence of the desirable agronomic trait inherited from the wild perennial *Glycine* species and selecting those plants that carry said trait;
thereby producing at least one $BC_3$ plant carrying the desirable agronomic trait inherited from the wild perennial *Glycine* species.

28. The method of claim 27 wherein said seeds of step (u) are cultured on a seed maturation medium comprising growth hormones to form callus, which produce embryos, said embryos subsequently producing shoots, which are rooted to produce plants.

29. The method of claim 27 wherein said desirable agronomic trait is selected from the group consisting of soybean nematode resistance, soybean rust resistance, bean pod mottle virus resistance and aphid resistance.

30. The method 27 of claim further comprising providing a plurality of said $BC_3$ plants carrying said trait, counting the number of chromosomes in said $BC_3$ plants and selecting those that have 40 paired domestic soybean chromosomes and less than the number of unpaired chromosomes as were present in said $BC_2$ parent plant, and testing the selected $BC_3$ plants for the presence of said desirable agronomic trait inherited from the wild perennial *Glycine* species to identify $BC_3$ plants that carry said trait.

31. The method of claim 1 further comprising selecting a desired backcrossed plant that is descended from a hybrid between a wild perennial *Glycine* ancestor and a domestic soybean variety ancestor wherein said plant has only one chromosome inherited from said wild perennial *Glycine* ancestor, said method comprising:
(i) producing a backcrossed plant that is descended from a hybrid between a wild perennial *Glycine* ancestor and a domestic soybean variety ancestor that has been successively backcrossed with at least three domestic soybean variety ancestors;
(j) counting the chromosomes of the backcrossed plant, and if it has 40 paired chromosomes inherited from domestic soybean and only one chromosome inherited from said wild perennial *Glycine* ancestor, selecting it as the desired plant; or (k) if the backcrossed plant has two or three chromosomes inherited from the wild perennial *Glycine* ancestor, selfing it and selecting progeny plants having 40 paired chromosomes inherited from domestic soybean and only one chromosome inherited from the wild perennial *Glycine* ancestor; or
(l) if the plant has more than three chromosomes inherited from the wild perennial *Glycine* ancestor, again backcrossing it with a plant of a domestic soybean variety and counting the chromosomes of the resulting further backcrossed plant; and
(m) continuing backcrossing the resulting plant from each backcross with a plant of a domestic soybean variety and counting the chromosomes of each resulting plant until a resulting plant is identified that has only one chromosome inherited from the wild perennial *Glycine* ancestor.

32. The method of claim 31 for producing a plurality of plants, each having a different single chromosome inherited from said wild perennial *Glycine* ancestor comprising identifying the single chromosome inherited from said wild perennial *Glycine* ancestor present in each plant and repeating the method of claim 30 until a plurality of plants with different single chromosomes inherited from said wild perennial *Glycine* ancestor has been produced.

33. The method of claim 32 wherein said plurality of plants collectively contain all the chromosomes present in said hybrid that were derived from said wild perennial *Glycine* ancestor.

34. The method of claim 31 also comprising testing each backcrossed plant for the presence of the agronomically desirable trait, and selecting only those plants carrying said trait for further backcrossing, thereby producing a desired plant having only one chromosome inherited from said wild perennial *Glycine* ancestor, wherein said trait is encoded on said one chromosome inherited from said wild perennial *Glycine* ancestor.

35. The method of claim 34 also comprising:
   (n) treating the plant of step (m) or seeds of said plant to cause recombination of said one chromosome inherited from said wild perennial *Glycine* ancestor with a chromosome inherited from said domestic soybean variety ancestor;
   (o) backcrossing the plant of step (n) with a plant of a domestic soybean variety;
   (p) testing the plant resulting from step (o) to identify the presence of the desired agronomic trait; and
   (q) counting the chromosomes of the plant of step (p), and if it has no unpaired chromosomes, selecting it for further breeding.

36. The method of claim 35 wherein said plant selected for further breeding is crossed with a plant of a domestic soybean variety that carries a further desirable agronomic trait, and said method includes selecting plants resulting from said cross that have inherited both said desirable agronomic trait of the wild ancestor and said further desirable agronomic trait.

37. The method of claim 36 wherein said further desirable agronomic trait is selected from the group consisting of desirable yield, lodging, plant height, field emergence, resistance or tolerance to herbicides, bacteria, fungi, viruses and nematodes; tolerance to drought, heat, chilling, freezing, excessive moisture, salt stress, oxidative stress; increased yields; food content and makeup; physical appearance; male sterility; drydown; standability; prolificacy; sugar properties; oil quantity and quality, and protein quantity and quality.

38. The method of claim 1 wherein said seed maturation medium of step (e) comprises:
   (a) major salts;
   (b) minor salts;
   (c) iron;
   (d) vitamins including L-glutamine;
   (e) growth hormones; and
   (f) sugar.

39. The method of claim 1 wherein said shoot regeneration medium of step (f) comprises:
   (a) major and minor salts, including less than about 2 g/L $NH_4^+$;
   (b) iron;
   (c) vitamins;
   (d) BAP; and
   (e) sugar.

* * * * *